US009486461B2

United States Patent
Petasis et al.

(10) Patent No.: US 9,486,461 B2
(45) Date of Patent: *Nov. 8, 2016

(54) METHODS AND COMPOSITIONS FOR INDUCING APOPTOSIS BY STIMULATING ER STRESS

(71) Applicant: UNIVERSITY OF SOUTHERN CALIFORNIA, Los Angeles, CA (US)

(72) Inventors: Nicos A. Petasis, Hacienda Heights, CA (US); Florence M. Hofman, Venice, CA (US); Stan G. Louie, Fullerton, CA (US); Thomas C. Chen, La Canada, CA (US); Axel H. Schonthal, Los Angeles, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/614,362

(22) Filed: Feb. 4, 2015

(65) Prior Publication Data
US 2016/0008378 A1  Jan. 14, 2016

Related U.S. Application Data

(60) Continuation of application No. 14/109,731, filed on Dec. 17, 2013, now abandoned, which is a continuation of application No. 13/160,291, filed on Jun. 14, 2011, now Pat. No. 8,637,564, which is a division of application No. 12/056,192, filed on Mar. 26, 2008, now Pat. No. 7,981,917.

(60) Provisional application No. 60/908,107, filed on Mar. 26, 2007.

(51) Int. Cl.
| | |
|---|---|
| *A61K 31/415* | (2006.01) |
| *A61K 31/635* | (2006.01) |
| *C12N 5/09* | (2010.01) |
| *G01N 33/50* | (2006.01) |
| *A61K 38/00* | (2006.01) |
| *A61K 31/4188* | (2006.01) |
| *A61K 38/05* | (2006.01) |
| *A61N 5/10* | (2006.01) |

(52) U.S. Cl.
CPC ........... *A61K 31/635* (2013.01); *A61K 31/415* (2013.01); *A61K 31/4188* (2013.01); *A61K 38/005* (2013.01); *A61K 38/05* (2013.01); *A61N 5/10* (2013.01); *C12N 5/0693* (2013.01); *C12N 5/0694* (2013.01); *G01N 33/5076* (2013.01); *C12N 2501/48* (2013.01); *G01N 2333/90245* (2013.01); *G01N 2333/914* (2013.01); *G01N 2510/00* (2013.01)

(58) Field of Classification Search
USPC ................................................ 514/406, 256
See application file for complete search history.

(56) References Cited

U.S. PATENT DOCUMENTS

| | | | |
|---|---|---|---|
| 5,756,530 A | 5/1998 | Lee et al. | 514/406 |
| 7,799,782 B2 * | 9/2010 | Munson | C07D 231/56 514/234.5 |
| 7,981,917 B2 * | 7/2011 | Schonthal | A61K 31/415 514/256 |
| 8,637,564 B2 * | 1/2014 | Petasis | A61K 31/415 514/256 |
| 2004/0033934 A1 | 2/2004 | Nichols et al. | |
| 2004/0156872 A1 | 8/2004 | Bosch et al. | |
| 2005/0026902 A1 | 2/2005 | Maziasz | |
| 2007/0009593 A1 | 1/2007 | Potter | |
| 2007/0010548 A1 | 1/2007 | Drees et al. | |

FOREIGN PATENT DOCUMENTS

| | | |
|---|---|---|
| JP | 2005-528384 A | 9/2005 |
| WO | WO 03/086287 A2 | 10/2003 |

OTHER PUBLICATIONS

Alex Schonthal, "Antitumor Properties of Dimethyl-Celecoxiib, a Derivatives of Celecoxib That Does Not Inhibit Cyclooxygenase-2: Implications for Glioma Therapy", Neurosurg Focus, vol. 20, No. 4, p. E21, 2006.

Zhu et al., "Using Cyclooxygenase-2 Inhibitors as Molecular Platforms to Develop a New Class of Apoptosis-Inducing Agents", Journal of the National Cancer Institute, vol. 94, No. 23, pp. 1745-1757, 2002.

Tsutsumi et al. "Endoplasmic reticulum stress response in involved in nonsteroidal anti-inflammatory drug-induced apoptosis", Cell Death and Differentiation, vol. 11, pp. 1009-1016, 2004.

Johnson et al., The cyclo-oxygenase-2 ihibitor celecoxib perturbs intracellular calcium by inhibiting endoplasmic reticulum Ca2'ATPases: a plausible link with its anti-tumor effect and cardiovascular risk, Biochem. J. vol. 366, pp. 831-837, 2002.

(Continued)

*Primary Examiner* — Rei-Tsang Shiao
(74) *Attorney, Agent, or Firm* — DLA Piper LLP (US)

(57) ABSTRACT

The present invention provides a method for inducing apoptosis in selected cells by aggravating ER-stress. The aggravation of ER-stress is achieved in a specific manner by inhibiting SERCA (sarcoplasmic/endoplasmic reticulum calcium ATPase), leading to elevated level of cytoplasmic calcium concentration, yet without inhibiting the activity of COX-2 (cyclooxygenase-2) or triggering the release of histamine. Induction of apoptosis may be enhanced by first inducing or further aggravating ER-stress through inhibition of proteasome or proteases. Also provided are compounds and compositions useful as ER-stress aggravating agents, methods for screening, selecting, identifying and designing the same and methods for treating diseased conditions by inducing apoptosis through specific and selective aggravation of ER-stress.

22 Claims, 26 Drawing Sheets

(56) References Cited

OTHER PUBLICATIONS

Namba et al., "Up-Regulation of 150-kDa Oxygen-Regulated Protein by Celecoxib in Human Gastric Carcinoma Cells", Mol Pharmacol, vol. 71, pp. 860-870, 2007.
Kang et al., "Enhancement of Glioblastoma Radioresponse by a Selective Box-2 Inhibitor celecoxib: Inhibition of Tumor Angiogenesis with Extensive Tumor Necrosis" International Journal of Radiation: Oncology Biology Physics, vol. 67, No. 3, pp. 888-896, Feb. 9, 2007.
Kang et al., "Combination celecoxib and temozolomide in C6 rat glioma orthotopic model" Oncology Reports 15, pp. 7-13, Jan. 1, 2006.
National Cancer Center, "View of NCT00112502 on Jun. 23, 2005; Phase II Randomized Study of Adjuvant Temozolomide Alone or in Combination with Thalidomide and/or Isotretinoin and/or Celecoxibin Patients Who Have Undergone Radiotherapy for Supratentorial Glioblastoma Multiforme" http://clinicaltrials.gov/archive/NCT00112502/2005_06_23 (retrieved on Sep. 21, 2011).
Extended European search report dated Sep. 30, 2011 for corresponding European application 087444083.9.
Namba et al., Molecular Pharmacology, Mar. 1, 2007, 71(3): 860-870.
Namba et al., CAS: 146:287908, 2007.
Kardosh et al., "Aggravated Endoplasmic Reticulum Stress as a Basis for Enhanced Glioblastoma Cell Killing by Bortezomib in Combination with Celecoxib or Its Non-Coxib Analogue, 2, 5-Dimethyl-Celecoxib", Cancer Research, vol. 68, No. 3, Feb. 1, 2008, pp. 843-851.
Extended European search report dated Oct. 28, 2015 for corresponding European application 15157373.

* cited by examiner

SEQUENCE LISTING

<160> NUMBER OF SEQ ID NOS: 6

<210> SEQ ID NO 1

-continued

```
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 1
caagcugacc cugaaguuct t                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 2
gaacuucagg gucagcuugt t                                              21

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 3
ggagcgcauu gauacuagat t                                              21

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 4
ucuaguauca augcgcucct t                                              21

<210> SEQ ID NO 5
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 5
aaguggccuc uucacaguca utt                                            23

<210> SEQ ID NO 6
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 6
aaaugacugu gaagaggcca ctt                                            23
```

METHODS AND COMPOSITIONS FOR INDUCING APOPTOSIS BY STIMULATING ER STRESS

CROSS-REFERENCE TO RELATED APPLICATIONS

The present application is a continuation of application Ser. No. 14/109,731 filed Dec. 17, 2013, which is a continuation of application of Ser. No. 13/160,291 filed Jun. 14, 2011, which is a divisional of application Ser. No. 12/056,192, filed on Mar. 26, 2008, the entire contents of which are incorporated herein by reference. This application also claims an invention which was disclosed in Provisional Application No. 60/908,107, filed Mar. 26, 2007, entitled "USE OF CHEMICAL COMPOUNDS TO STIMULATE THE ENDOPLASMIC RETICULUM (ER) STRESS RESPONSE IN TUMOR CELLS CAUSING TUMOR CELL DEATH". The benefit under 35 USC §119(e) of the United States provisional application is hereby claimed. The above priority application is hereby incorporated herein by reference.

FIELD OF THE INVENTION

The invention pertains to the field of molecular medicine. More particularly, the invention pertains to methods, compounds, and compositions for selectively inducing apoptosis in cells by aggravating the ER stress response. The invention also relates to methods for the treatment of cancer, including difficult to treat, drug-resistant, and recurring cancer.

BACKGROUND OF THE INVENTION

Apoptosis is a process involving programmed cell death or "cellular suicide" and under physiological conditions it occurs after cell surface death receptors are occupied or activated by various genotoxic agents. This process leads to mitochondrial release of cytochrome C, which in turn activates the caspase enzymes that promote apoptosis.

Since apoptosis was first described in 1972 by Kerr et al. (1), much knowledge has been accumulated about this important cellular process. Although a comprehensive understanding of apoptosis at the molecular level and cellular level is yet to be achieved, the knowledge accumulated thus far has led to the realization that because the process is genetically programmed, it may be susceptible to the effects of mutation and, therefore, may be involved in the pathogenesis of a variety of human diseases such as viral infections, autoimmune diseases and cancer (2, 3). Based on this realization, it has been widely recognized that any therapeutic strategy aimed at specifically triggering apoptosis in diseased cells that suffer from disregulation of apoptosis (e.g. cancer) may deliver potentially promising therapies.

In a recent article, Ferreira et al. (4) have reviewed current strategies for exploiting the therapeutic potentials of apoptosis. To summarize the review, existing strategies for apoptosis-based therapies can be grouped into two types: the proapoptotic approaches and the apoptosis-permissive approaches. Table 1 shows a list of exemplary approaches in each category.

The proapoptic approaches are strategies that aim to directly induce apoptosis. They try to achieve apoptosis through exploitation of existing cellular players and pathways such as death receptors and caspases, or the introduction of exogenous proapoptotic molecules such as Apoptin. Proapoptotic strategies can involve: (a) direct introduction of proapoptotic players; (b) modulation of antiapoptotic molecules; or (c) restoration of tumor suppressor gene function. However, proapotic strategies are not based on structural differences between normal and cancer cells. Therefore, achieving tumor cell specificity, while minimizing toxicity, poses a major challenge in the development of this type of approaches For example, experimental therapies targeting death receptors such as TNF and Fas have resulted in ischemic and hemorrhagic lesions in several tissues.

The apoptosis-permissive approaches, on the other hand, is based on the premises that by blocking some of the intricate signaling pathways mediating survival messages that in normal conditions contribute to keep the cellular homeostasis, apoptosis may be triggered. This type of strategies do not have the non-specific toxicity problems of the proapoptotic approaches, however, successful development of this type of strategies is highly dependent on a detailed knowledge of the mechanisms by which apoptosis is facilitated. Thus far, our understanding and knowledge of such mechanisms leading to the secondary effect of apoptosis are still incomplete.

Therefore, there still exists a need for new strategies to selectively induce apoptosis in diseased cells, and new tools and methods for implementing the same.

SUMMARY OF THE INVENTION

Accordingly, one object of the present invention is to provide a method for inducing apoptosis that may serve as the basis for new therapies.

A further object of the present invention is to provide compounds and compositions that are useful as apoptosis inducing agents.

Another further object of the present invention is to provide a method for screening, selecting, and discovering compounds that are useful as agents for inducing apoptosis.

Yet another further object of the present invention is to provide apoptosis-based treatment methods for treating diseases.

These and other objects of the present invention, which will become more apparent in conjunction with the following detailed description of the preferred embodiments, either along or in combinations thereof, have been satisfied by the unexpected discovery of a new endoplasmic reticulum (ER)-stress response mechanism which leads to apoptosis.

In a first aspect, the present invention provides a method of inducing or aggravating stress in a cell's ER to trigger apoptosis. Embodiments according to this aspect of the present invention generally include the steps of selectively inhibiting sarcoplasmic/ER calcium ATP-ase (SERCA) activity in the cell without inhibiting cyclooxygenase-2 (COX-2) activity; and elevating the expression of CCAAT/ enhancer binding protein homologous transcription factor, also called GADD153: growth arrest and DNA damage-inducible gene 153 (CHOP) in the cell. The combination of inhibiting SERCA activity and elevating CHOP expression results in a condition favorable for initiation of apoptosis in the cell.

In a second aspect, the present invention provides a method for screening, selecting, or designing compounds useful for inducing or aggravating ER stress in a cell to trigger apoptosis in the cell. Embodiments according to this aspect of the present invention generally include the steps of obtaining information about a test compound and identifying the test compound as a potential ER-stress aggravating agent if the compound is an inhibitor of SERCA, and is not an inhibitor of COX-2.

In a third aspect, the present invention provides compounds useful as an ER stress aggravating agent, having the general formula:

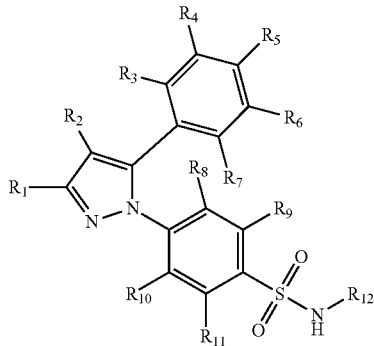

wherein, $R_1$ is methyl, fluoromethyl, difluoromethyl, trifluoromethyl, alkyl, fluoroalkyl, difluoroalkyl, trifluoroalkyl, polyfluoroalkyl, hydroxyalkyl, or carboxyalkyl;

$R_2$ is hydrogen, fluoro, chloro, bromo; fluoromethyl, difluoromethyl, trifluoromethyl, alkyl, fluoroalkyl, difluoroalkyl, trifluoroalkyl, polyfluoroalkyl, hydroxyalkyl, or carboxyalkyl;

$R_3$-$R_7$ are independently selected from a group consisting of: hydrogen, fluoro, chloro, bromo, alloxy, alkyl, fluoroalkyl, difluoroalkyl, trifluoroalkyl, polyfluoroalkyl, hydroxyalkyl, or carboxyalkyl, aryl and heteroaryl;

$R_8$-$R_{11}$ are independently selected from a group consisting of: hydrogen, fluoro, chloro, bromo; fluoromethyl, difluoromethyl, trifluoromethyl, alkyl, fluoroalkyl, difluoroalkyl, trifluoroalkyl, polyfluoroalkyl, hydroxyalkyl, carboxyalkyl, alkenyl, alkynyl, cycloalkyl, heterocyclic, aryl, or heteroaryl; and $R_{12}$ is hydrogen, acetyl, acyl, alkyl, fluoroalkyl, difluoroalkyl, trifluoroalkyl, polyfluoroallcyl, hydroxyalkyl, carboxyalkyl; aminoacyl, aminoalkyl, cycloalkyl, heterocyclic, aryl, or heteroaryl.

In a fourth aspect, the present invention also provides a pharmaceutical composition useful for inducing or aggravating ER stress in a cell to trigger apoptosis in the cell. Embodiments according to this aspect of the present invention generally include an ER-stress aggravating agent; and a pharmaceutically acceptable carrier.

In a fifth aspect, the present invention also provides a method for treating a diseased condition in a patient by inducing or aggravating ER stress in selected diseased cells to trigger apoptosis in the cells. Embodiments according to this aspect of the present invention generally include the steps of: administering a pharmaceutically effective amount of a pharmaceutical composition according to the previous aspect of the present invention.

Other aspects and advantages of the invention will be apparent from the following description and the appended claims.

Total cellular lysates were prepared and analyzed by Western blot analysis with specific antibodies to CHOP. As a control for equal loading, all blots were also analyzed with antibodies to actin (only one of these control blots is shown at the bottom). The tumor type of each cell line is indicated on the right.

Figure 4:
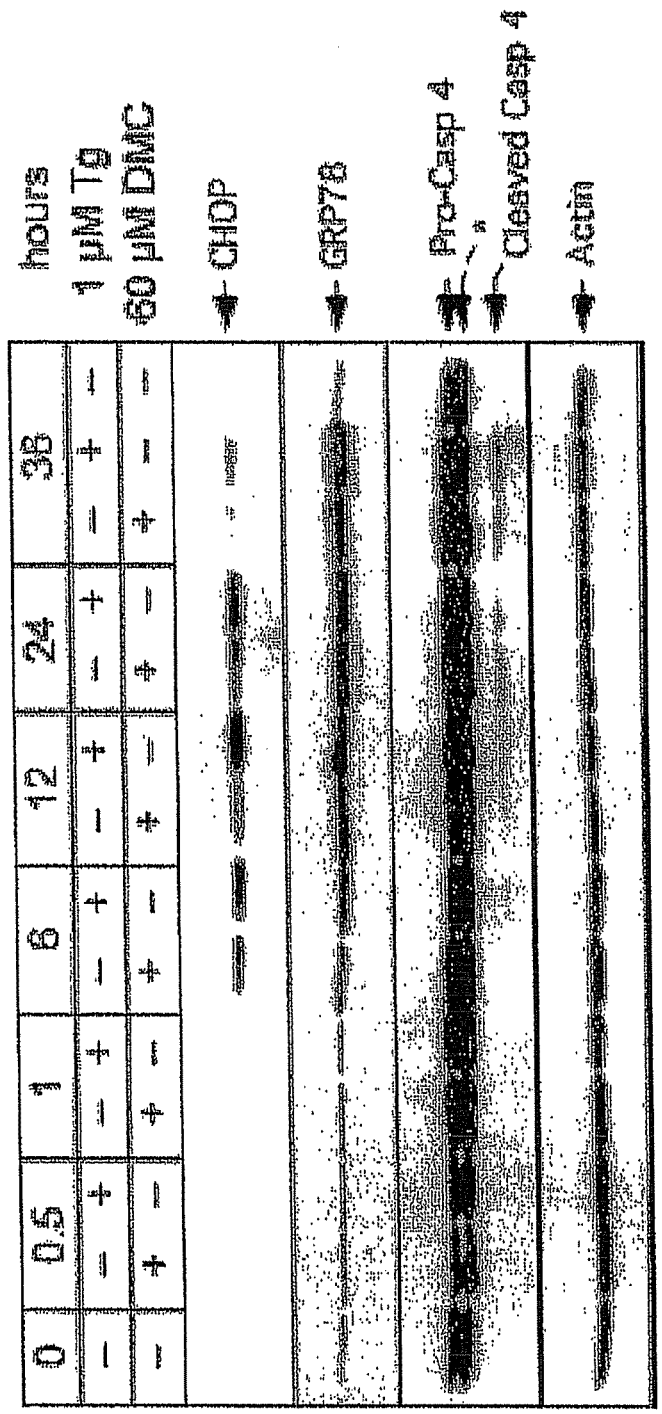

FIG. 4 shows that ER stress indicators are induced similarly by DMC and thapsigargin. U251 glioblastoma cells were cultured in the presence of 1 µM thapsigargin (Tg) or 60 µM DMC for various times, as indicated. Total cell lysates were prepared and analyzed by Western blot with specific antibodies to the ER stress proteins GRP78, CHOP, and caspase 4 (Casp 4). Actin was used as a loading control. Pro-casp 4 denotes the inactive caspase 4 proenzyme, whereas Cleaved Casp 4 is indicative of the activated form of this enzyme; * refers to a faster-migrating band that is inconsistently observed in these Western blots.

Figure 5:
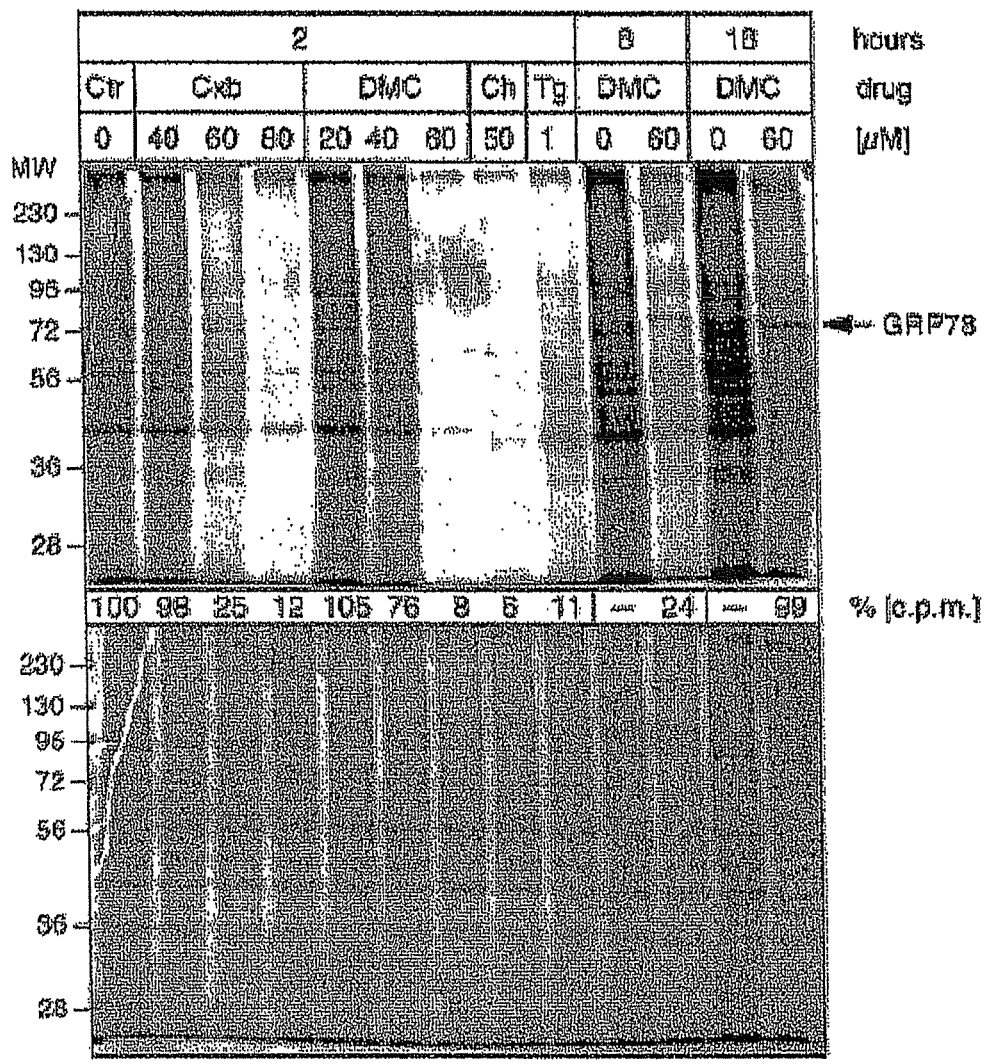

FIG. 5 shows that DMC and celecoxib, but not other coxibs or NSAIDs, induce calcium release into the cytoplasm. (A) U251 cells were treated with DMC or various coxibs and NSAIDs, and changes in intracellular calcium levels were recorded as described in Materials & Methods. The top two panels show the typical spikes of calcium increase that were consistently observed in response to DMC or celecoxib treatment. The third panel shows the typical response (i.e., lack thereof) to valdecoxib, rofecoxib, flurbiprofen, indomethacin, and sulindac (only shown for valdecoxib). Arrows indicate timepoint of drug addition. (B) Chart shows the average (mean±SD) calcium increase in response to treatment with the various drugs from several repeats. Essentially similar results were also obtained with the LN229 cell line.

Figure 6:
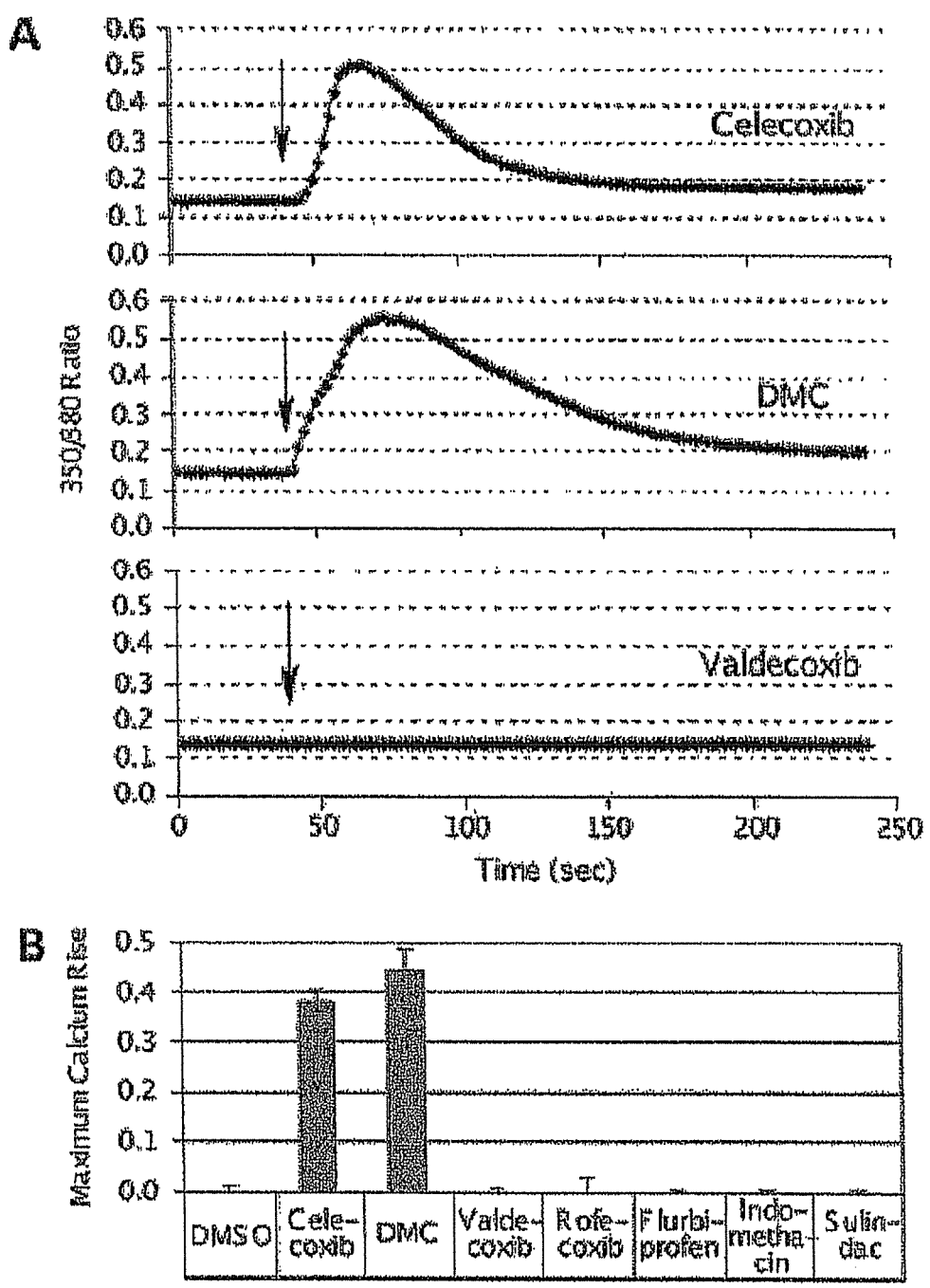

FIG. 6 shows that the induction of CHOP and GRP78 is specific to celecoxib and DMC. U251 glioblastoma cells were cultured in the presence of DMC, celecoxib, rofecoxib, or valdecoxib, and the protein levels of CHOP and GRP78 were determined by Western blot analysis. Shown are (A) time kinetics at 50 µM of each drug, and (B) concentration dependence after 15 hours of incubation. Bgr. refers to a background signal that is inconsistently observed with the GRP78 antibody. All blots were processed in parallel, so that signal intensity is directly comparable among the different panels. Note that DMC is the most potent stimulant, whereas rofecoxib and valdecoxib are inactive under these conditions.

Figure 7A:
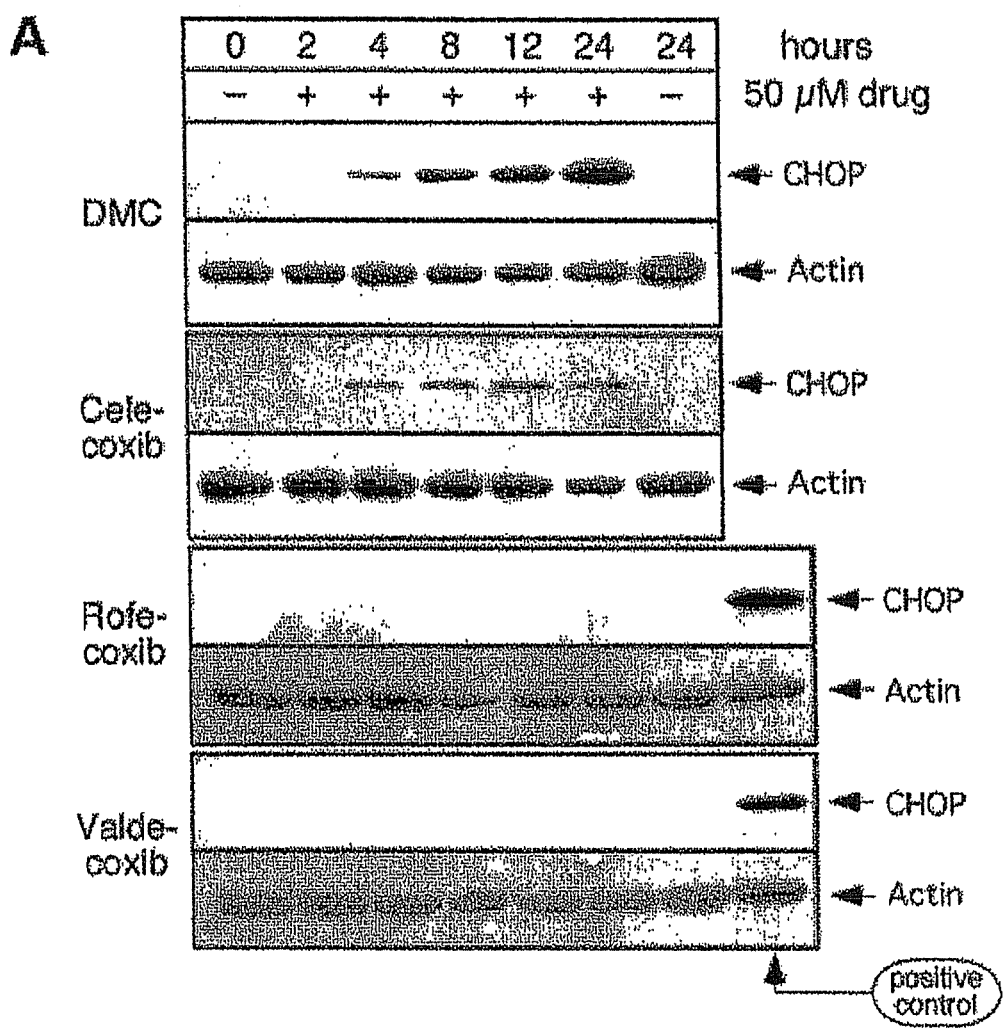
Figure 7B:
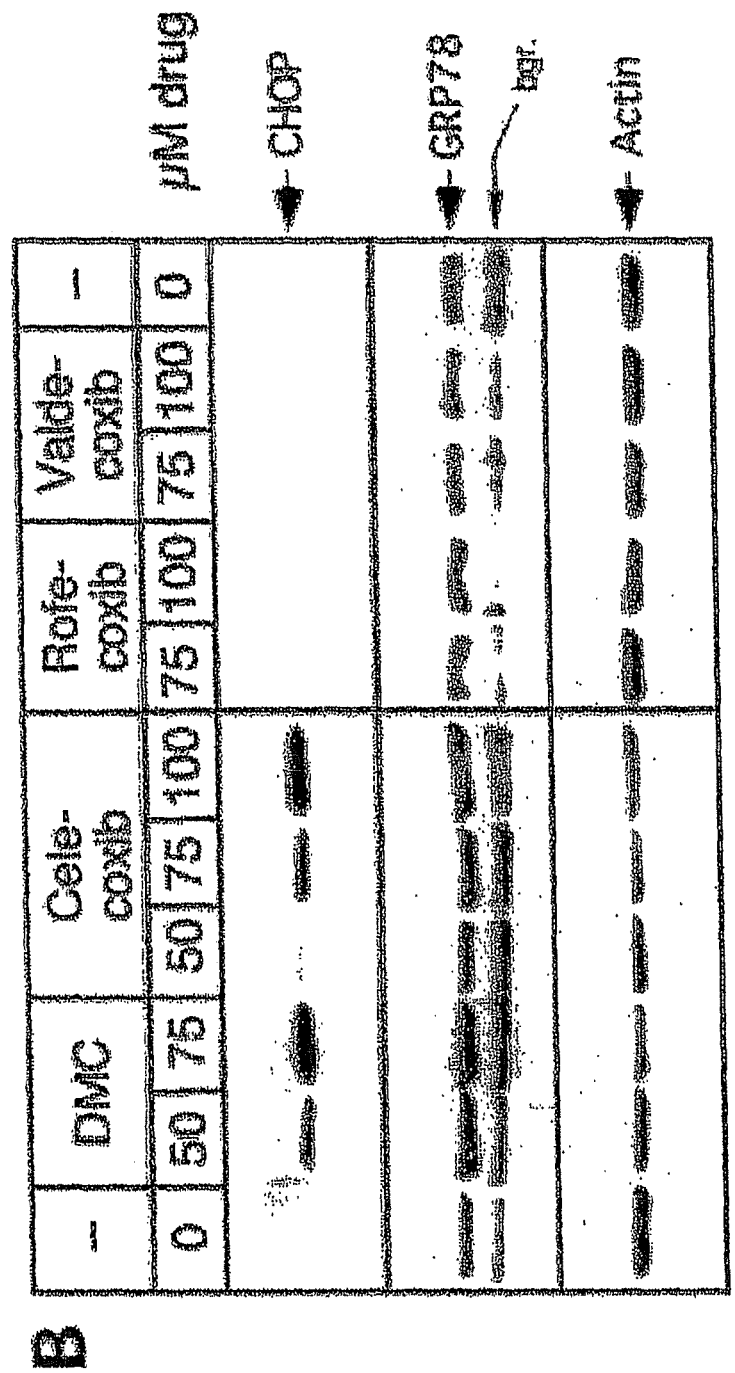
Figure 7C:
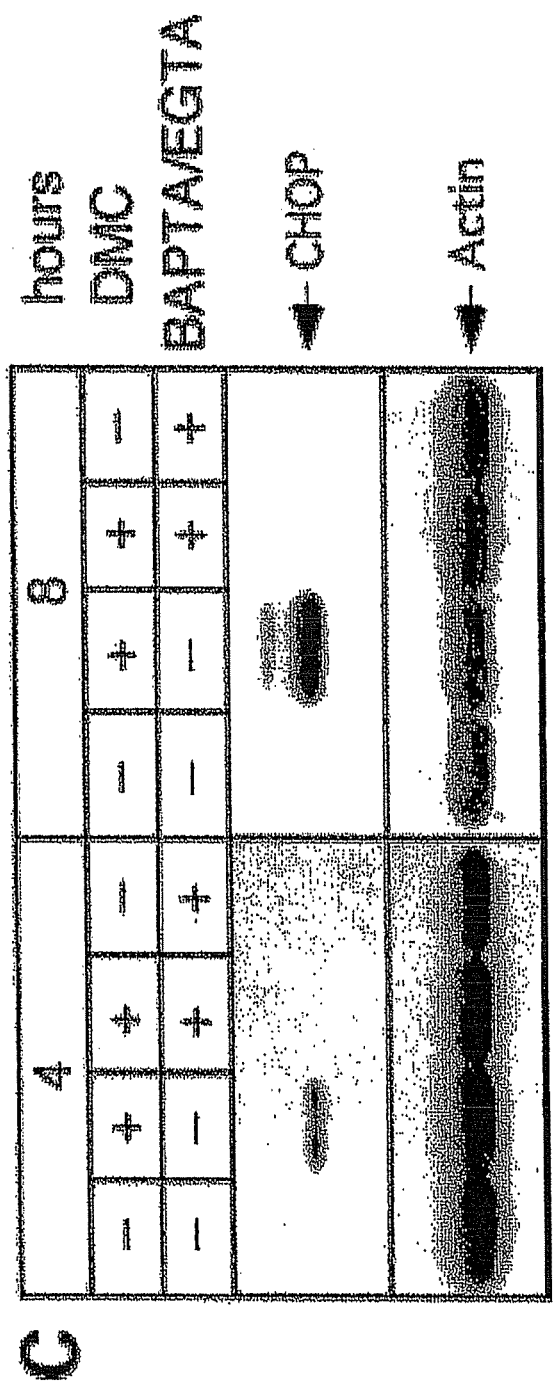

FIGS. 7A-7C show that the induction of CHOP and GRP78 is specific to celecoxib and DMC and requires calcium. U251 glioblastoma cells were cultured in the presence of DMC, celecoxib, rofecoxib, or valdecoxib, and the protein levels of CHOP and GRP78 were determined by Western blot analysis. Shown are (FIG. 7A) time kinetics at 50 µM of each drug, and (FIG. 7B), concentration dependence after 15 hours of incubation. Bgr. refers to a background signal that is inconsistently observed with the GRP78 antibody. In (FIG. 7C), cells were treated with 60 µM DMC in the presence or absence of 20 µM BAPTA-AM and 0.78 mM EGTA, both of which are potent chelators of $Ca^{2+}$. All blots in A and B were processed in parallel, so that signal intensity is directly comparable among the different panels.

Figure 8A:
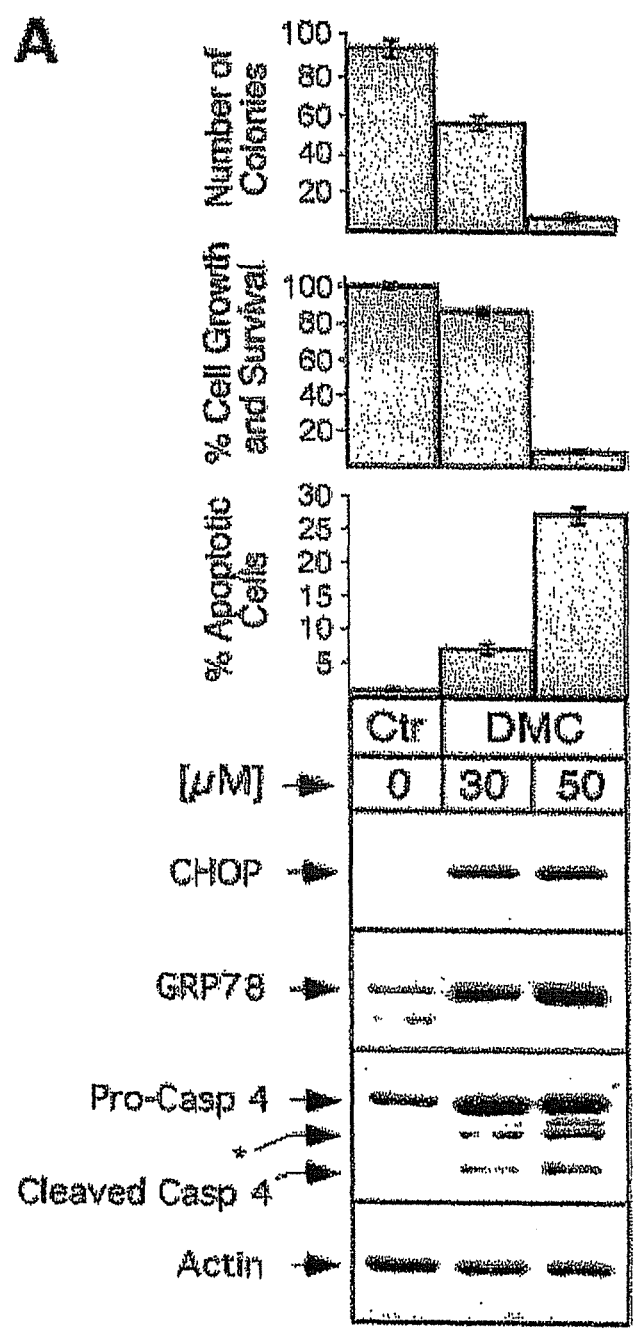
Figure 8B:
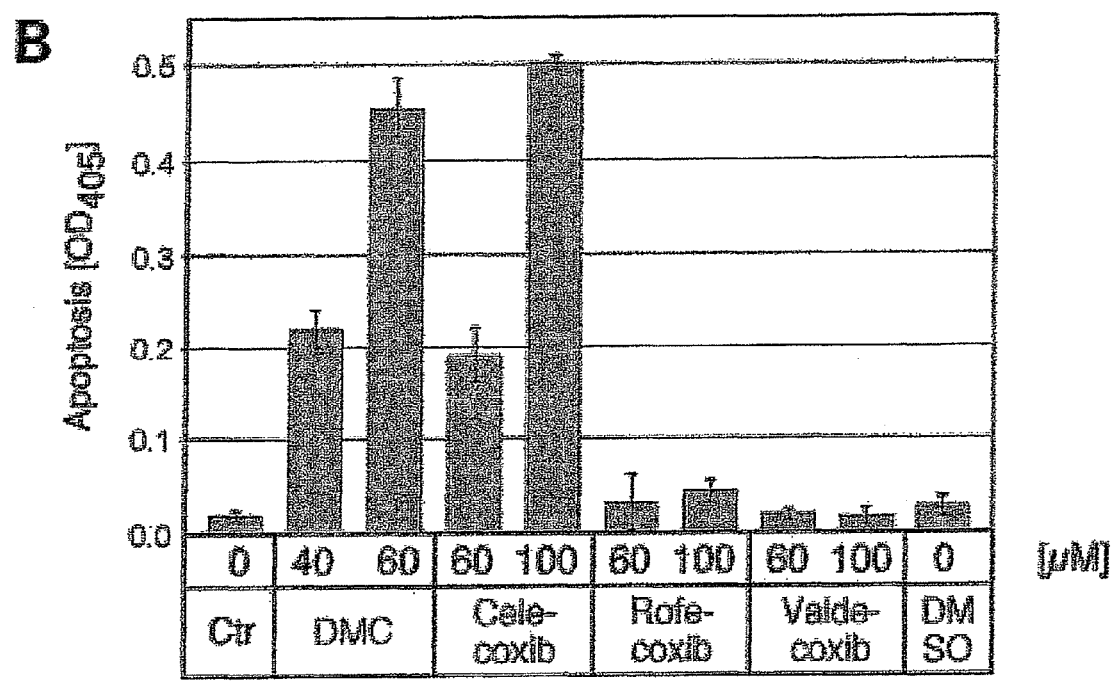
Figure 8C:
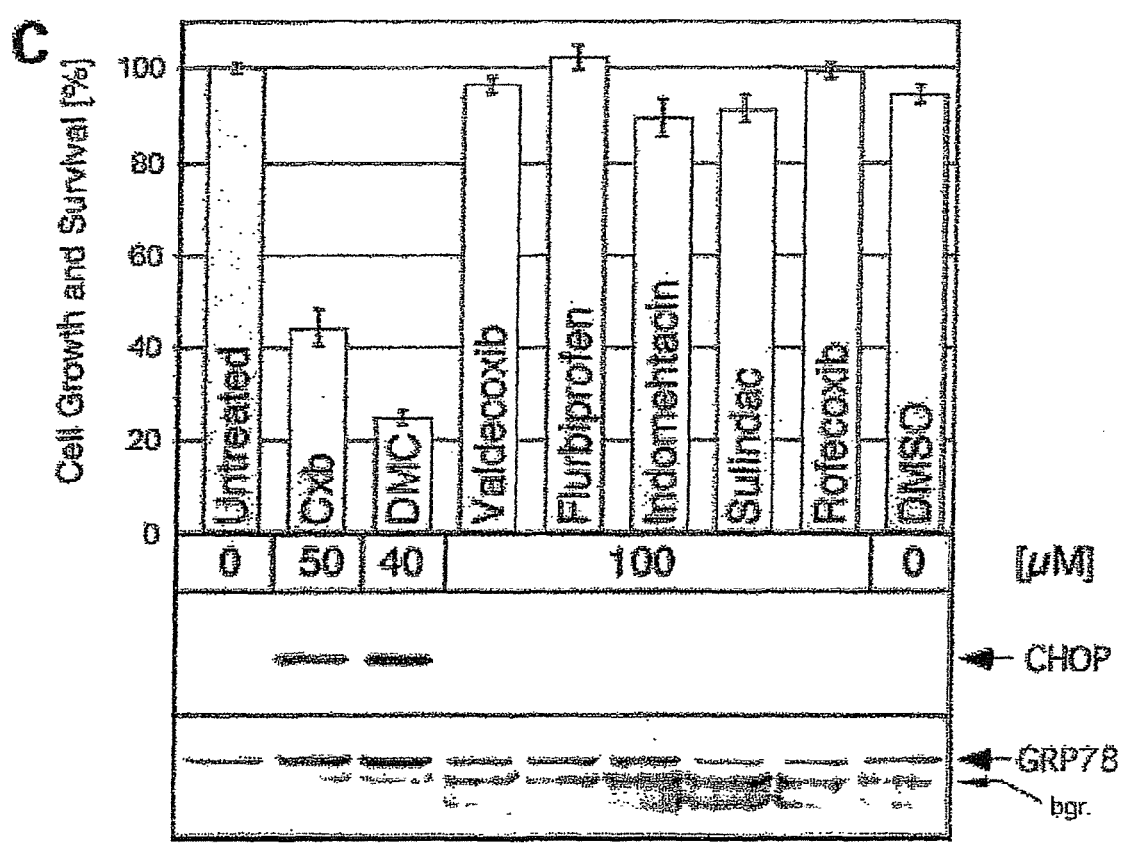

FIGS. 8A-8C show that the induction of CHOP and GRP78 correlates with increased apoptosis and reduced cell growth and survival. U251 glioblastoma cells were treated with different drugs, and various parameters of cell growth and cell death were comparatively analyzed. As controls, cells remained either non-treated (Co) or were treated with the solvent DMSO alone. (FIG. 8A) Cells were treated with 30 or 50 µM DMC for 48 hours and the effects on cell growth/survival and on cell death were determined by various assays. The panel labeled Number of Colonies displays the results from a colony forming assay, where the absolute number of surviving cells able to spawn a colony of newly grown cells was determined. The panel labeled % Cell Growth and Survival shows the results of conventional MTT assays performed at the end of the 48-hour drug treatment period. The panel labeled % Apoptotic Cells presents the percentage of cells undergoing apoptosis as revealed by the TUNEL assay after 48 hours of drug treatment. Below the three panels, the expression levels of the ER stress indicators CHOP, GRP78, and caspase 4 at the end of the 48 hour drug treatment is shown, as determined by Western blot analysis with specific antibodies (actin served as a loading control. (FIG. 8B) Cells were treated with various concentrations of different drugs for 48 hours, as indicated, and cell death was measured with the cell death ELISA kit. (FIG. 8C) Cells were treated with DMC or various coxibs and traditional NSAIDs for 48 hours, as indicated, and cell growth and survival was determined with the conventional MTT assay (control, non-treated cells were set at 100%). MTT assays were performed in 96-well plates with the use of $3.0-8.0 \times 10^3$ cells per well as described in detail elsewhere (34). In parallel, the expression levels of CHOP and GRP78 protein were determined by Western blot analysis. Note that DMC is the most potent drug, celecoxib is substantially weaker, and none of the other coxibs or traditional NSAIDs are active under these conditions.

Figure 9:
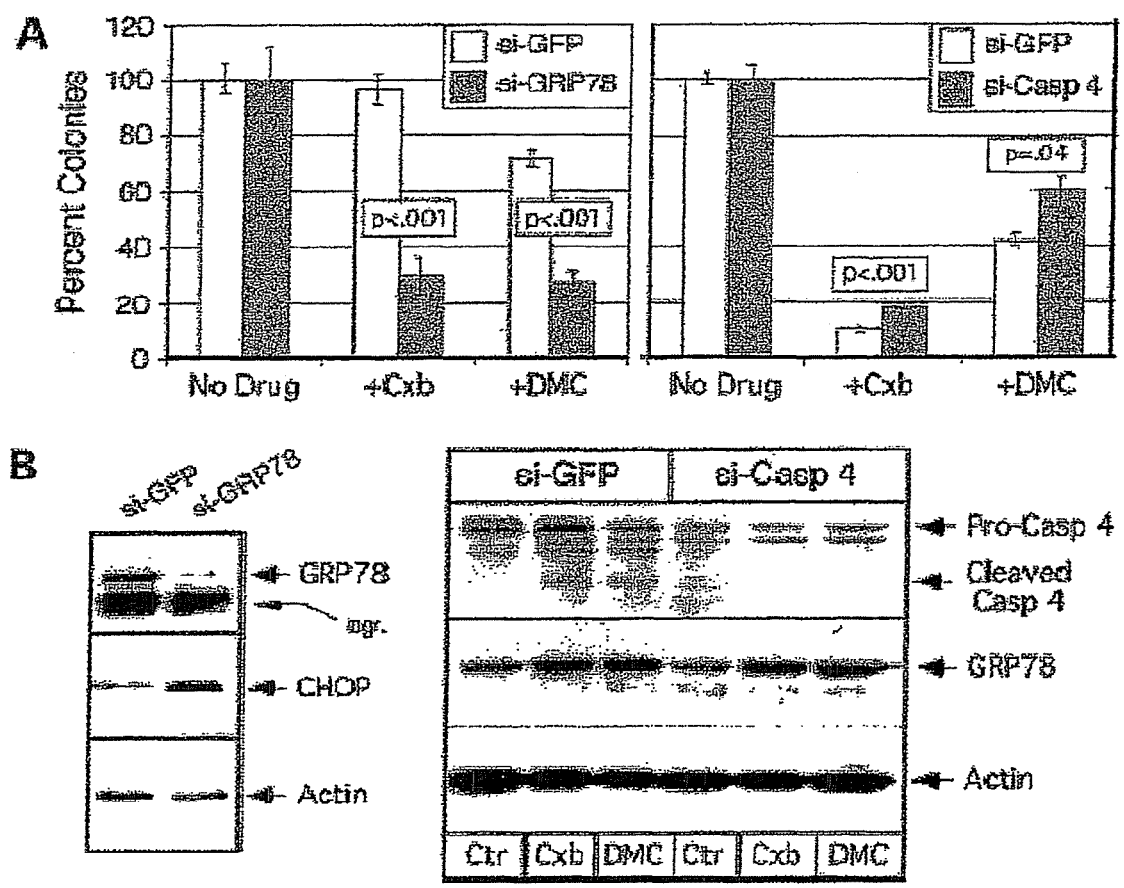

FIG. 9 shows that the knock-down of GRP78 enhances, whereas knock-down of Caspase 4 reduces, cell killing by celecoxib and DMC. U251 glioblastoma cells were transiently transfected with si-RNA directed at GRP78 (si-GRP78) or caspase 4 (si-Casp 4). As a control, an siRNA targeted at green fluorescent protein (si-GFP) was used. (A) Seventy-two hours after transfection, parallel cultures were treated with 40 celecoxib (Cxb) and 30 µM DMC in the case of si-GRP78/si-GFP, or with 60 µM Cxb and 40 µM DMC in the case of si-Casp 4/si-GFP; in all instances, control cultures received no drug treatment or treatment with solvent (DMSO) alone. After 48 hours of drug treatment, the drugs were removed and the fraction of surviving cells was determined by colony forming assays. Shown is the percentage of surviving cells (where the number of colonies under non-drug treated conditions was set to 100%). The p-values shown demonstrate statistically significant differences in survival between cells receiving si-GRP78 and control siRNA (si-GFP), and between cells receiving si-Casp 4 and control si-RNA, respectively. (B) In order to verify the effectiveness of the si-RNAs, Western blot analysis of the target proteins was performed. Note that the knock-down of GRP78 leads to increased levels of CHOP protein, as expected from the model of ER stress, where GRP78 signaling is upstream of CHOP. Caspase 4 si-RNA also down-regulates its target (and cleaved caspase 4 becomes undetectable), but does not affect the induction of GRP78 in response to celecoxib or DMC, as expected from the ER stress model, where caspase 4 is downstream of GRP78 signaling.

Figure 10:
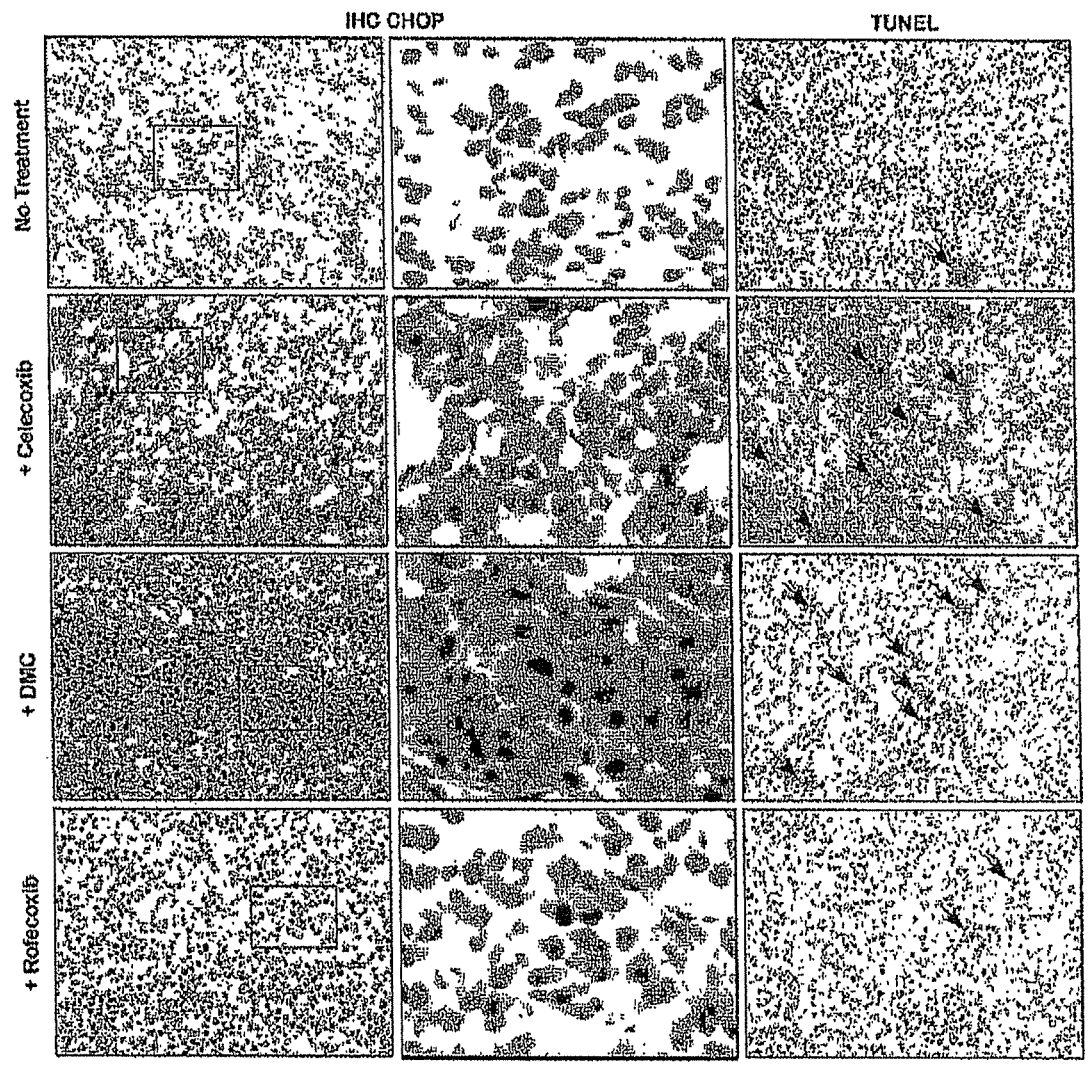

FIG. 10 shows that DMC and celecoxib, but not rofecoxib, stimulate ER stress response and apoptosis in tumor cells in vivo. Nude mice were implanted subcutaneously with U87 glioblastoma cells. Once tumors had reached a volume of 500 mm³, two animals each received either DMC or rofecoxib (150 mg/kg), or no drug for 36 hours. Thereafter, all six animals were sacrificed and their tumors analyzed by immunohistochemical staining for CHOP protein, as well as by TUNEL assay for cell death/apoptosis. Left panels: expression of CHOP protein (small black rectangles denote enlarged areas of the same photograph shown in the middle panels). Right panels: cell death (arrows indicate examples of TUNEL-positive, i.e., apoptotic, cells). The entire experiment was repeated with increasing daily dosages of drugs (including celecoxib) for 50 hours (see Materials & Methods), and similar results were obtained. In all cases, representative sections are shown.

Figure 11:
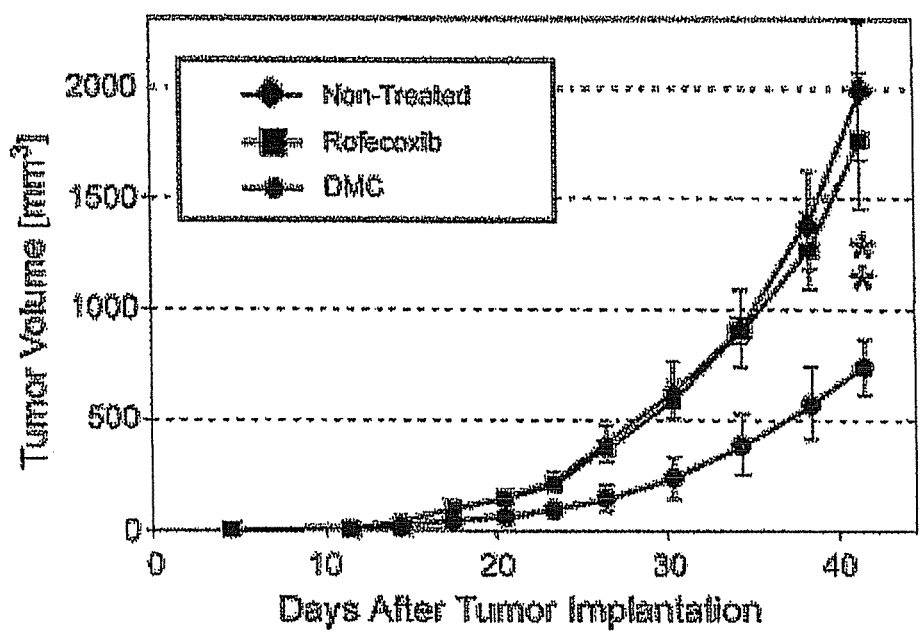

FIG. 11 shows that DMC, but not rofecoxib, inhibits tumor growth in vivo. Nude mice were implanted subcutaneously with U87 glioblastoma cells. Once palpable tumors had formed, the animals received daily chow supplemented with DMC, rofecoxib, or no drug. Tumor size was determined every three days. Shown is the average (mean±SD) tumor volume in each group (n=5). Asterisks (**): p<0.01 between control and DMC-treated animals on day 42.

Figure 12A:
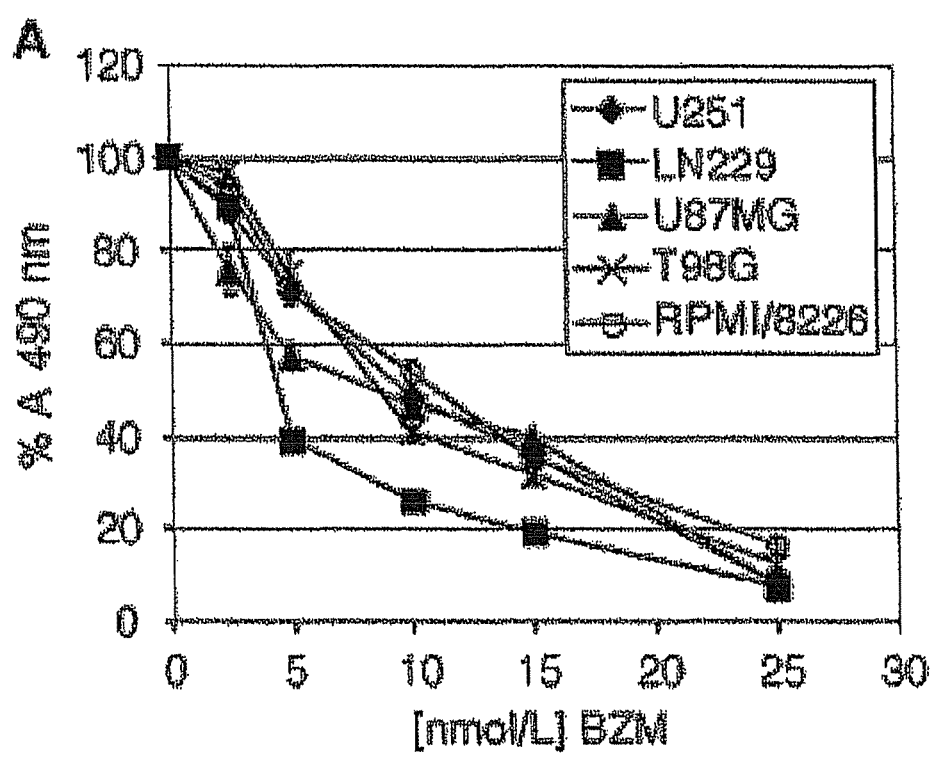
Figure 12B:
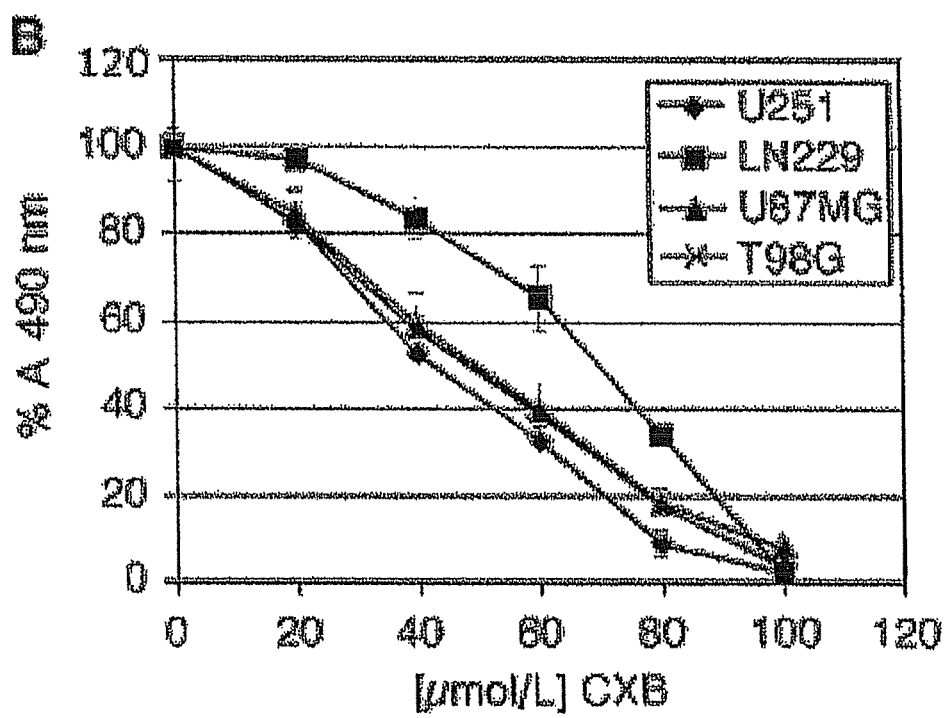
Figure 12C:
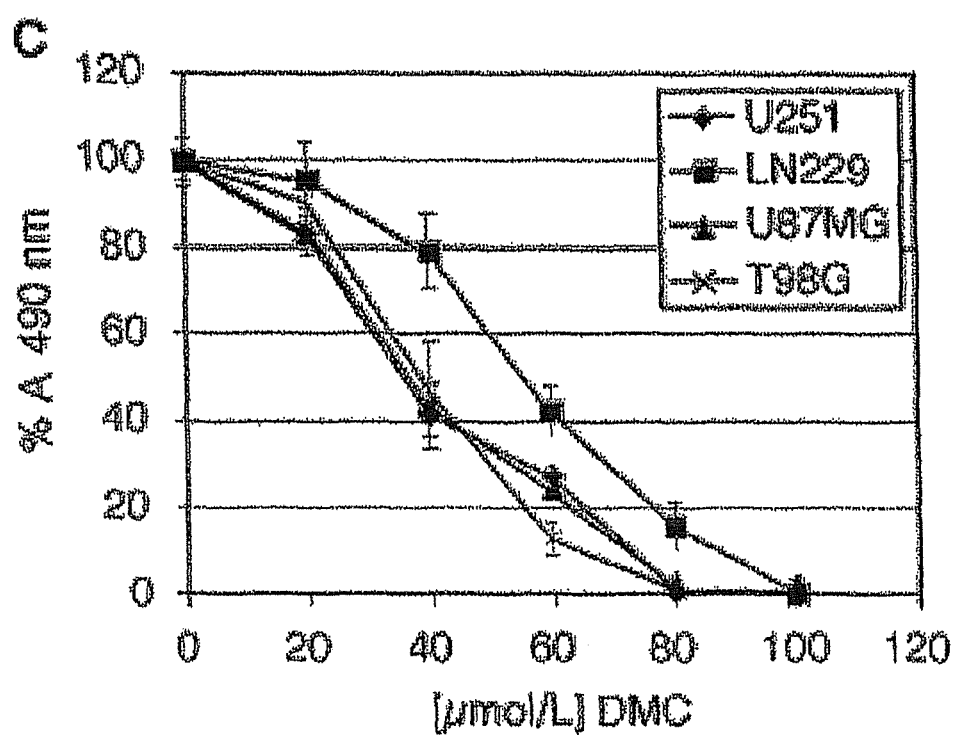

FIGS. 12A-12C show that bortezomib, celecoxib, and DMC reduce glioblastoma cell survival. Cell growth and survival of various glioblastoma cell lines was determined by MTT assay after 48 hours of culture in the presence of increasing concentrations of (FIG. 12A) bortezomib (BZM), (FIG. 12B) celecoxib (CXB), or (FIG. 12C) 2,5-dimethyl-celecoxib (DMC). For comparison purposes to the known anti-multiple myeloma effects of bortezomib, the RPMI/8226 multiple myeloma cell line was included in (A).

Figure 13:
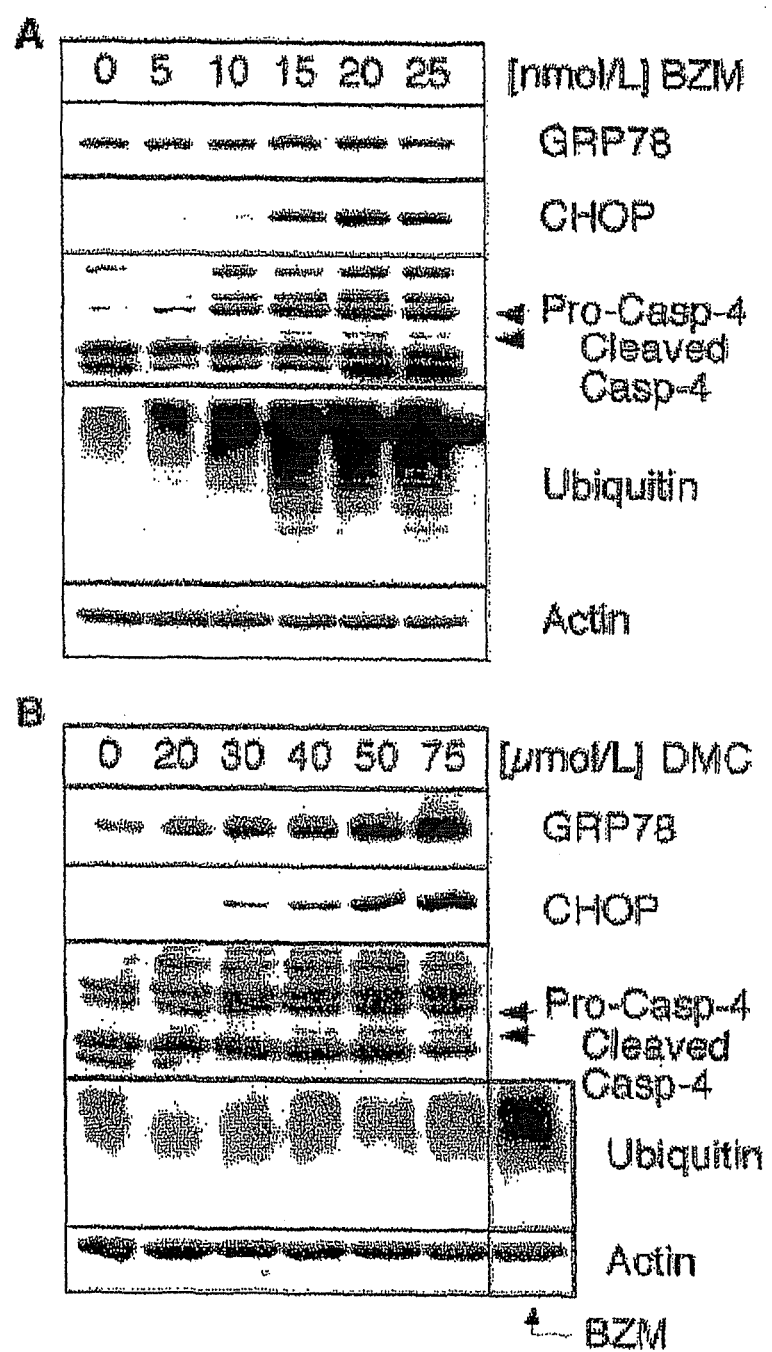

FIG. 13 shows that DMC and bortezomib induce indicators of ER stress. U251 glioblastoma cells were cultured for 24 hours in the presence of increasing concentrations of (A) bortezomib (BZM) or (B) DMC. Total cell lysates were analyzed by Western blot with specific antibodies to ubiquitin, GRP78, CHOP, and caspase 4. Actin was used as a loading control. Pro-casp-4 denotes the inactive caspase 4 proenzyme, whereas cleaved casp-4 is indicative of the activated form of the enzyme. For comparison purposes, cells treated with 10 nM bortezomib were analyzed side-by-side to DMC-treated cells in (B), indicating that the amount of ubiquitination is much more prevalent in bortezomib-treated cells than in DMC-treated cells. Note that in the caspase 4 blots several non-specific background bands were observed (consistent with similar observations in the literature); the specific bands were identified with the use of various controls (not shown) and comparison to the literature.

Figure 14:
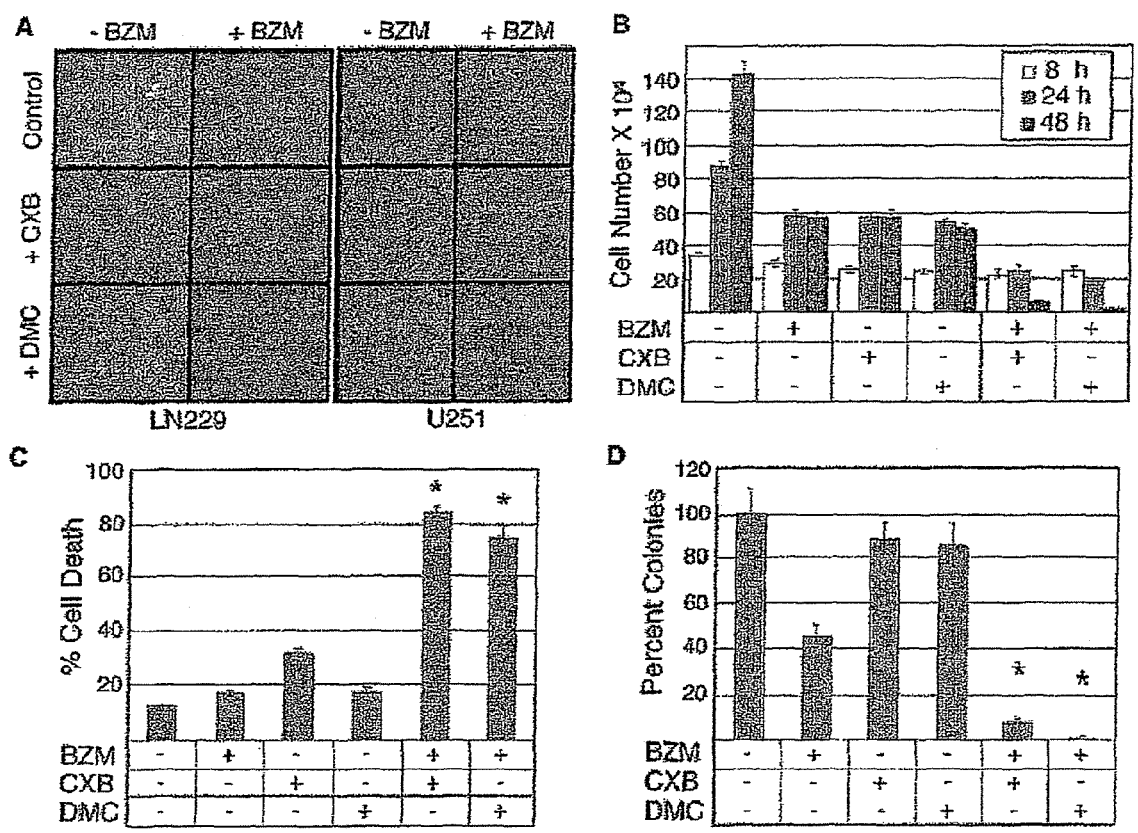

FIG. 14 shows that celecoxib and DMC enhance growth inhibition and cell death by bortezomib. Glioblastoma cell lines were treated with bortezomib (BZM), celecoxib (CXB), or DMC alone and in combination. (A) Photomicrographs depicting the effects of combined drug treatment in LN229 and U251 cells after 48 hours of drug treatment. Representative sections are shown. (B) Quantitative analysis of combination drug effects. LN229 cells were treated with drugs as above for 8, 24, and 48 hours. Cell viability was determined by trypan blue exclusion assay. The assays were performed with triplicate samples, and results are representative of three independent experiments. Shown is the number of viable cells under each condition (mean±SD). (C) U87MG cells were cultured for 24 hours in the presence of drugs as indicated, and the extent of cell death was determined by cell death ELISA (shown as mean percent; n=4; ±SD). (D) LN229 cells were treated with drugs for 48 hours and the number of long-term surviving cells that were able to spawn a colony was determined two weeks thereafter (colony formation assay). Shown is the percentage (mean±SD) of surviving cells from triplicate experiments. The number of colonies obtained from non-drug treated controls was set at 100%. In A-D, the following drug concentrations were used: LN229: 5 nM BZM, 60 µM CXB, 40 µM DMC; U251: 10 nM BZM, 50 µM CXB, or 30 µM DMC; U87MG: 5 nM BZM, 50 µM CXB, 35 µM DMC. Asterisk indicates that the difference between individual drug treatments and combination drug treatments was statistically highly significant (p<0.001).

Figure 15:
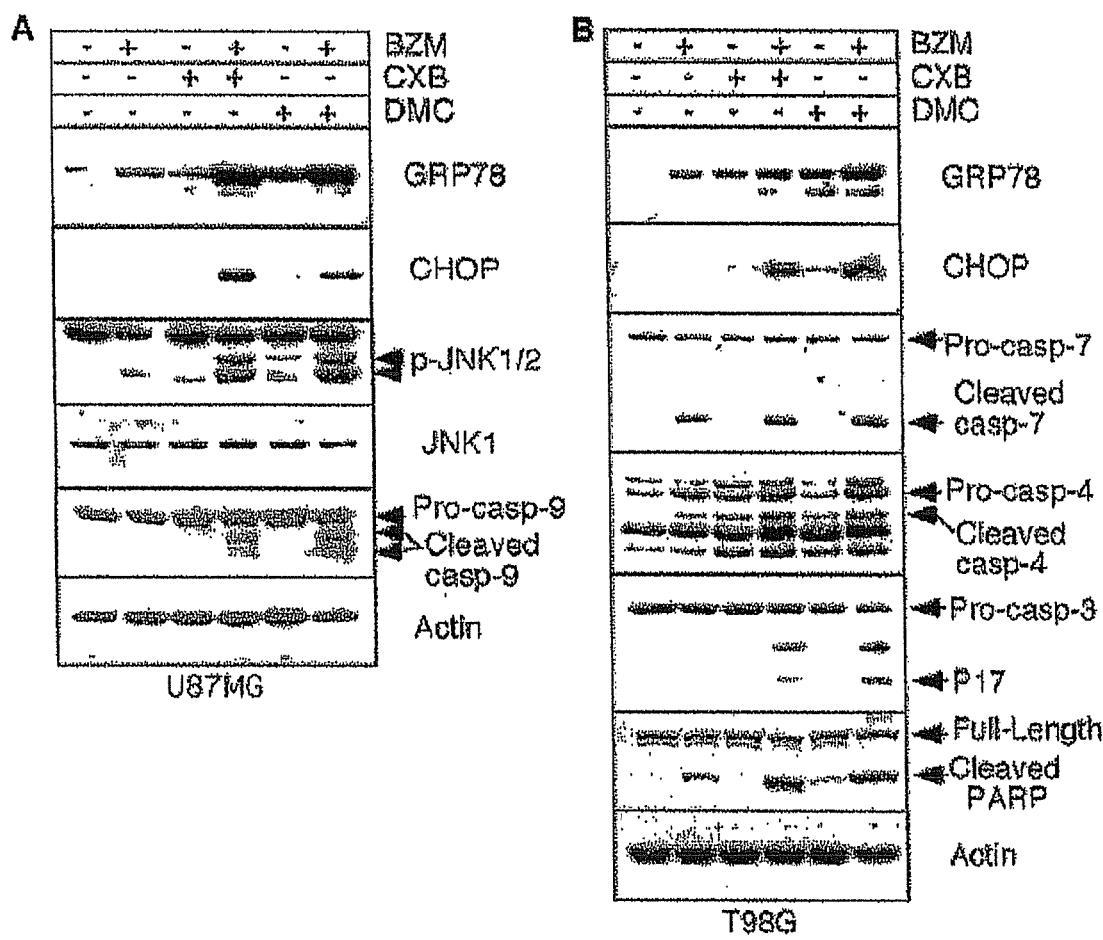

FIG. 15 shows that celecoxib and DMC enhance upregulation of indicators of ER stress and apoptosis by bortezomib. (A) U87MG and (B) T98G cells were cultured in the presence of 10 nM bortezomib (BZM), 50 µM celecoxib (CXB), or 35 µM DMC individually or in combination as indicated for 24 hours. Total cell lysates were analyzed by Western blot with specific antibodies to GRP78, CHOP, caspase-3 (Casp-3), caspase-4 (Casp-4), caspase-7 (Casp-7), caspase-9 (Casp-9), PARP and JNK, as indicated. Actin was used as a loading control. Pro-caspase denotes the full-length (inactive) caspase proenzymes, whereas cleaved caspases represent the activated forms of these enzymes. The activity of JNK1 and JNK2 was determined with the use of an antibody that specifically recognizes JNK phosphorylated on Thr183/Tyr185 (p-JNK1/2). Equal amounts of JNK1 were confirmed with an antibody that reacts with all JNK forms present.

Figure 16:
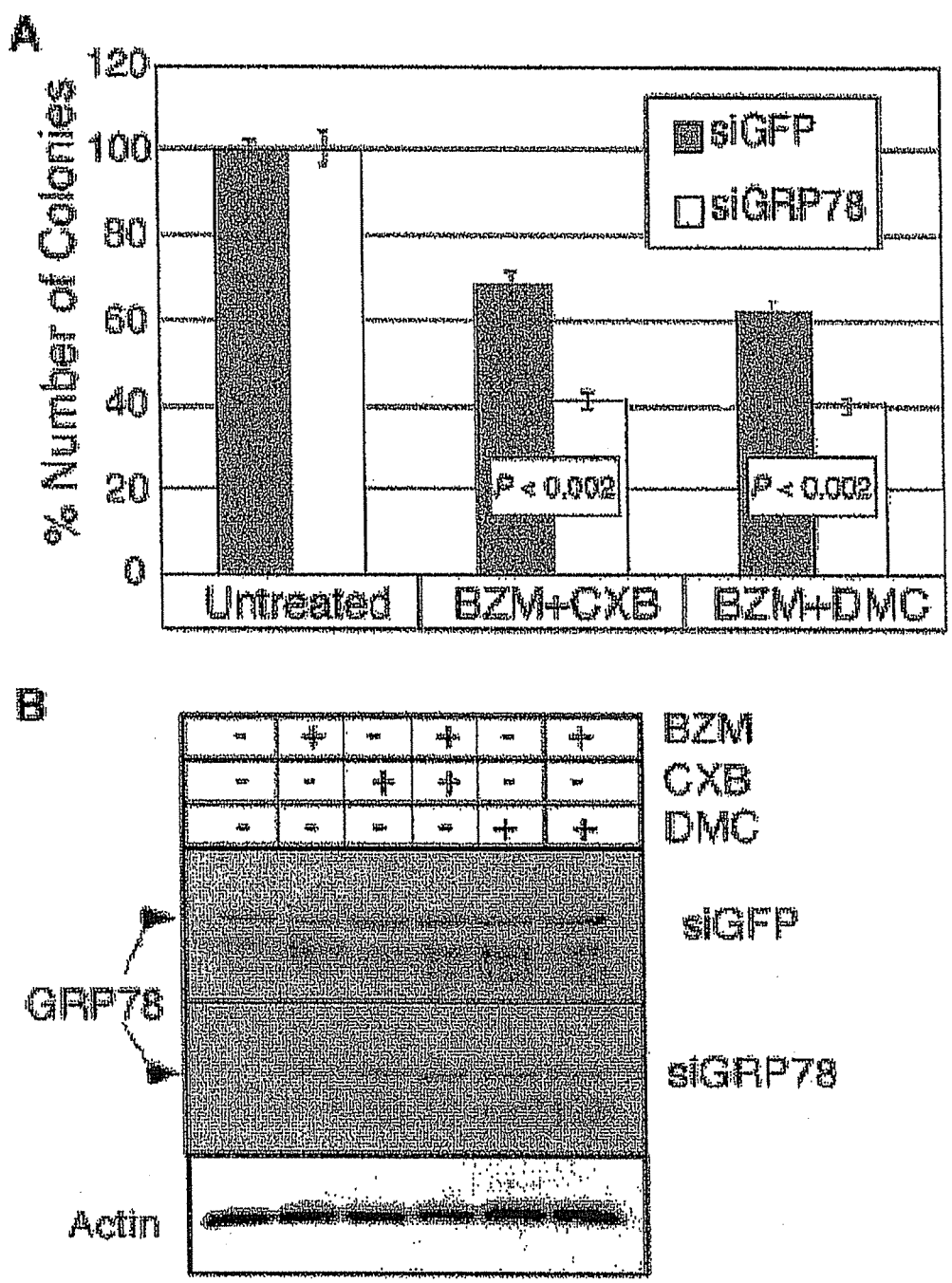

FIG. 16 shows that knock-down of GRP78 enhances cell killing by combination drug treatment. U251 cells were transiently transfected with si-RNA directed at GRP78 (si-GRP78). As a control, an siRNA targeted at green fluorescent protein (si-GFP) was used. (A) Seventy-two hours after transfection, parallel cultures were treated with 5 nM bortezomib (BZM) combined with either 25 µM celecoxib (CXB) or 15 µM DMC. In parallel, transfected control cultures received no drug treatment or treatment with solvent (DMSO) alone. After 48 hours, the drugs were removed and the fraction of surviving cells was determined by colony forming assays over the course of 12-14 days. Shown is the percentage of surviving cells able to spawn a colony (where the number of colonies under non-drug treated conditions was set to 100%). The reduction in colony numbers in drug-treated siGRP78-transfected versus drug-treated siGFP-transfected cells was statistically significant (p<0.002). (B) In order to verify the effectiveness and specificity of the transfected si-RNAs, Western blot analysis of GRP78 expression was performed from siGFP-transfected and from siGRP78-transfected cells treated with the respective drugs in parallel. Both of these blots were processed and developed simultaneously, and therefore can be directly compared side-by-side. Although the down-regulation of GRP78 by its siRNA was not 100% effective, the levels of this protein nonetheless were consistently lowered in each condition as compared to the matching control cells transfected with siGFP. Of note, overall lower concentrations of each drug were used in this experiment to enable the detection of further enhanced cell death by siRNA pretreatment.

Figure 17A:
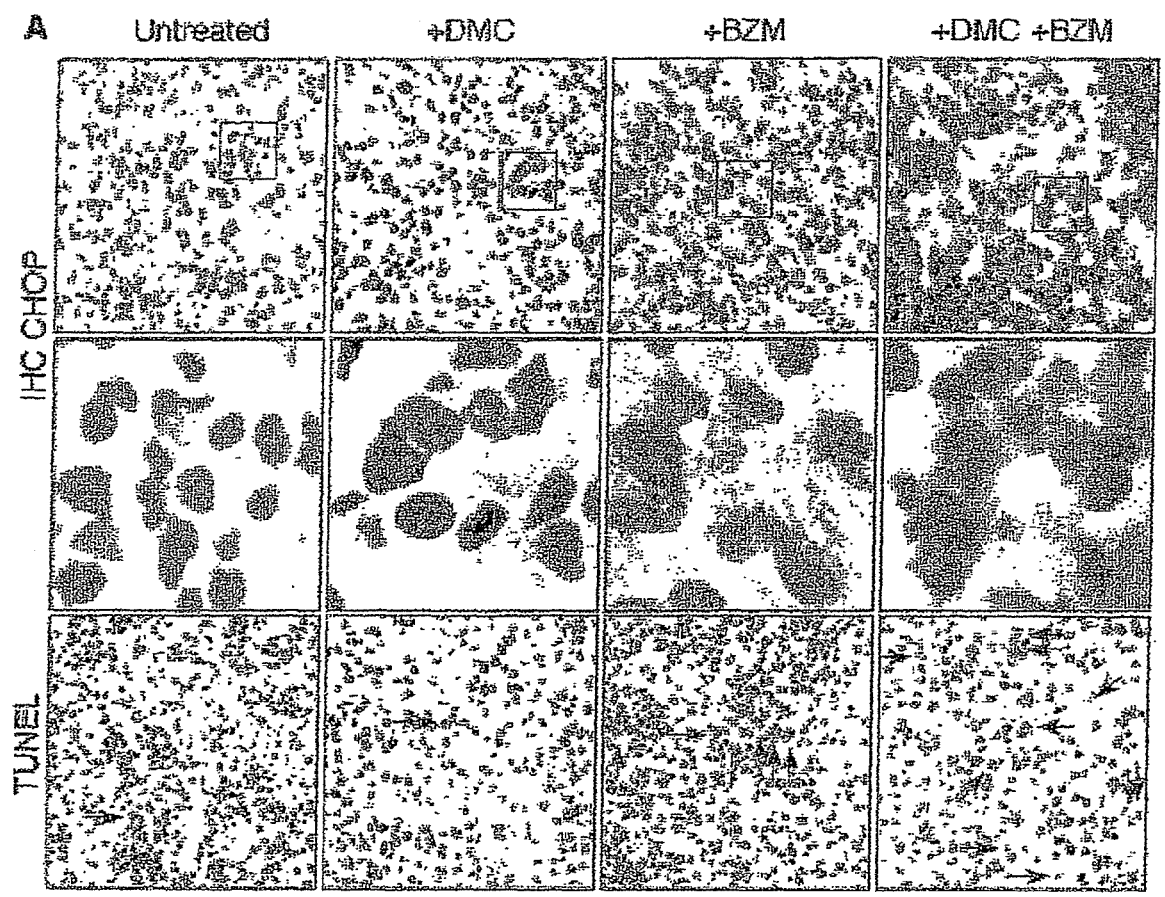
Figure 17B:
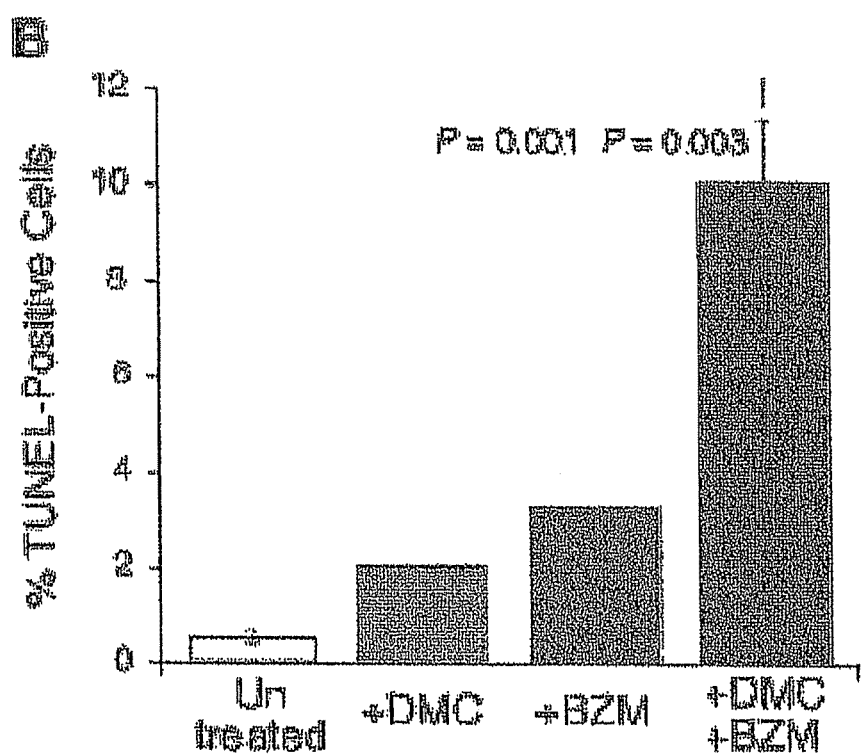

FIGS. 17A-17B show that DMC enhances bortezomib's effects on ER stress and apoptosis in vivo. Tumor-bearing mice were treated with 1 mg/kg bortezomib (BZM) and 7.5 mg/kg DMC individually or in combination, or remained untreated. Fifty hours later, the animals were sacrificed and the tumors analyzed by immunohistochemical staining for CHOP (ER stress indicator) or by TUNEL (apoptosis indicator). (FIG. 17A) The top panels show tumor tissue stained with CHOP antibodies, and the middle panels show enlarged areas (indicated by the small rectangles) of the same sections. The bottom panels display TUNEL staining; a few select TUNEL-positive cells are indicated by arrows. (FIG. 17B) The percentage of TUNEL-positive cells (as indicated by reddish-brown stain) was determined in ten randomly chosen microscopic fields from each treatment group and is presented as mean±SD. Statistically significant differences in the extent of tumor cell death between individual and combination drug treatments are indicated in the chart.

Figure 18:
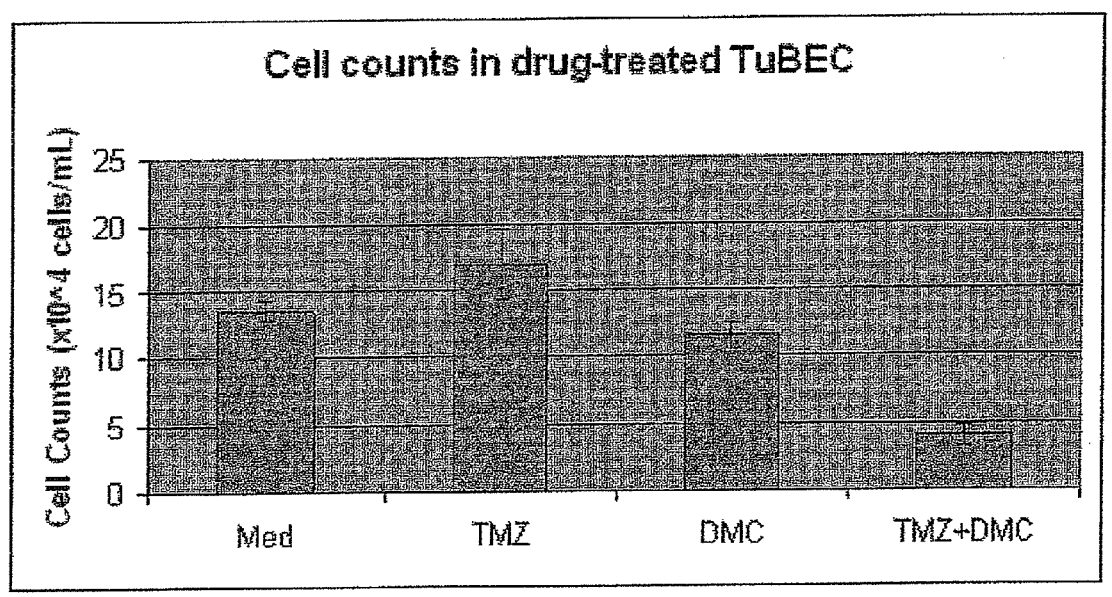

FIG. 18 shows the synergistic effect between Temozolomide (TMZ), the standard of treatment for gliomas, and the non-coxib celecoxib analogue, 2,5-dimethyl-celecoxib (DMC) that acts via aggravated ER Stress. The results show enhanced cell killing of tumor-associated brain endothelial cells (TuBEC) that were treated with a combination of TMZ (300 uM) and 20 uM DMC for 48 hours. After drug treatment the cells were incubated for another 12 days in the absence of drug, in order to determine their long-term survival; at that time cytotoxicity was evaluated using the trypan blue exclusion technique. Results are presented as number of viable cells per group.

Figure 19:
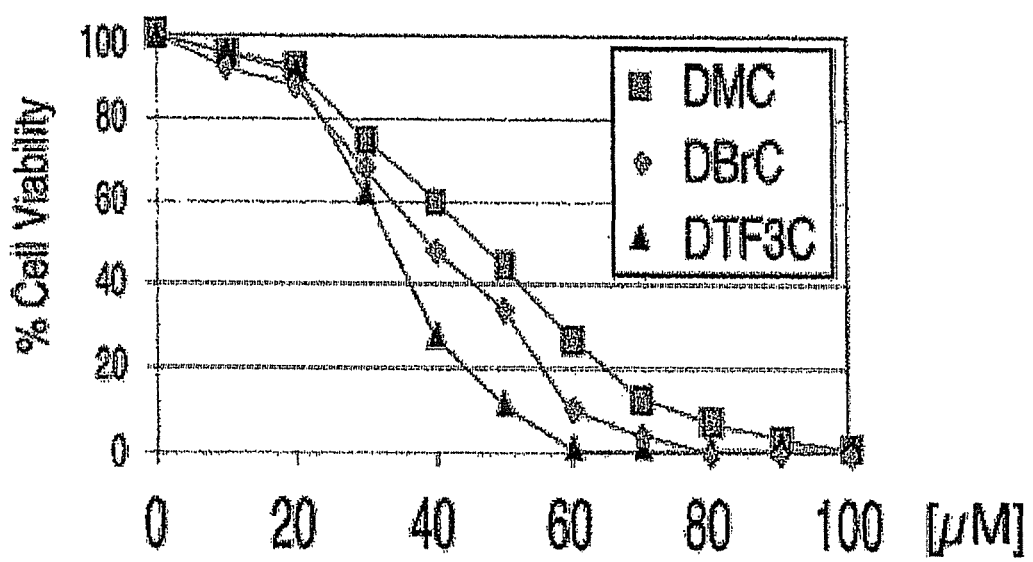

FIG. 19 shows the relative ability of three related derivatives in accordance with embodiments of the present invention to induce apoptosis in human glioblastoma cells. The most potent compound was the 2,5-ditrifluoromethyl derivative (DTF3C).

DETAILED DESCRIPTION

As set forth in the summary, the present invention is based on the unexpected discovery of a new strategy for using the ER-stress response mechanism to induce apoptosis. In accordance with the strategy of the present invention, embodiments of the present invention provide methods and tools for implementing the strategy. Specifically, the present invention provides a new class of chemotherapeutic compounds capable of modulating endoplasmic reticulum stress (ESR) that induces apoptosis (cell death) in both actively proliferating and quiescent cancer cells. These compounds also inhibit tumor invasion, vasculogenesis, and angiogenesis. Moreover, these compounds are characterized by high bioavailability (including the CNS), exhibit little toxicity, can be administered orally, and may be combined with standard chemotherapeutic agents for enhanced anticancer effect. Therapeutic methods according to some aspects of the present invention are aimed at treating cancer as a living entity, not as a collection of aberrant cells, and may be applied to all cancers.

Although not intending to be limited to any particular theory, a brief discussion of the ER stress response mechanism is provided herein to facilitate a full and complete understanding of the strategy of the present invention.

Model of ER-Stress Response

The endoplasmic reticulum (ER) stress response (ESR) consists of a set of adaptive pathways that can be triggered by disparate perturbations of normal ER function, such as accumulation of unfolded proteins, lipid or glycolipid imbalances, or changes in the ionic conditions of the ER lumen (see (5, 6) for reviews). The primary purpose of the ESR is to alleviate stressful disturbance and restore proper ER homeostasis; however, in the case of intense or persistent ER stress, these pathways will trigger programmed cell death/apoptosis. One of the central pro-survival regulators of the ESR is glucose-regulated protein 78 (GRP78/BiP), which has important roles in protein folding and assembly, in targeting misfolded protein for degradation, in ER $Ca^{2+}$-binding, and in controlling the activation of trans-membrane ER stress sensors (7). On the other hand, CCAAT/enhancer binding protein homologous transcription factor (CHOP/GADD153) and caspase 4 are critical executioners of the pro-apoptotic arm of the ESR (8, 9).

Figure 1:
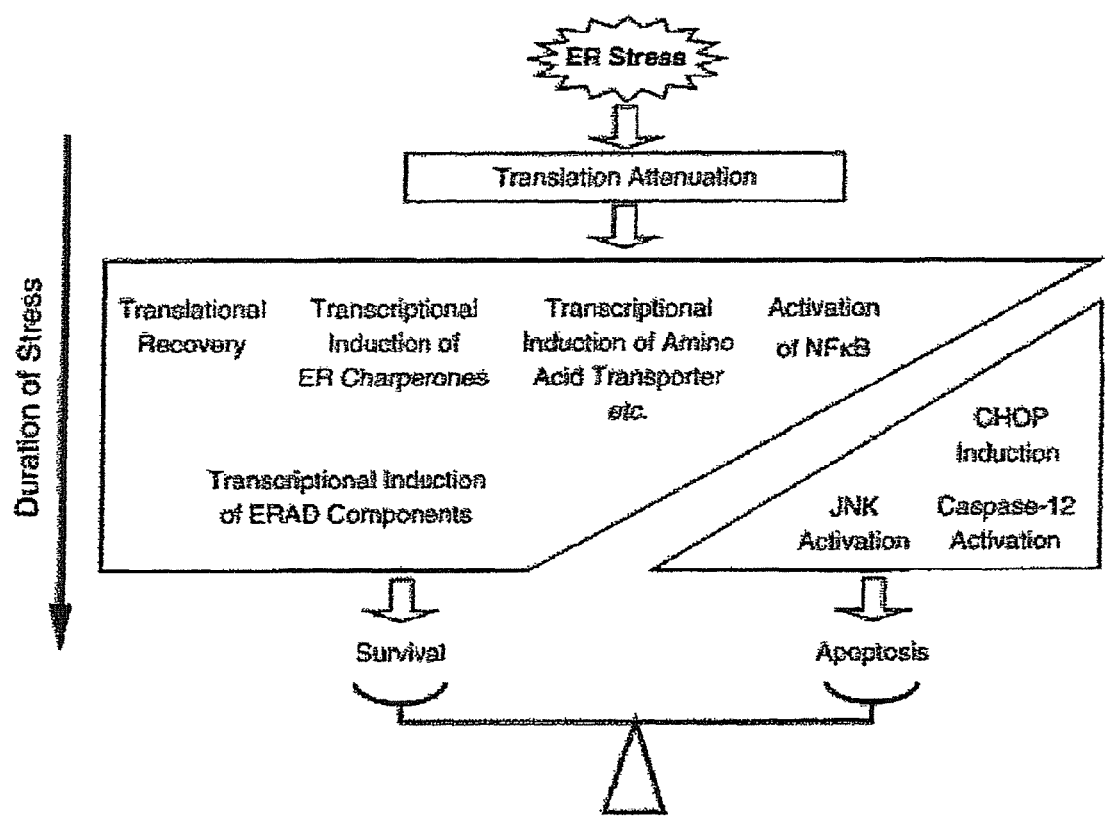
FIG. 1 shows a simplified model of the critical events during the ER stress response. In case of severe ER stress (such as after the inhibition of SERCA) translational attenuation ensues and participates in the subsequent events of the ER stress response (ESR). The ESR is constituted of two antagonistic parts: (1) protective components (listed in the left box) that execute defensive processes to ensure cellular survival under stress, and (2) pro-apoptosis (death-inducing) components (listed in the right box), which will begin to dominate and trigger cell death (apoptosis) if stress becomes too excessive or cannot be relieved (such as in the continuous presence of a SERCA inhibitor). In case of low-level/chronic ER stress, as is frequently present in tumor cells, components in the left box maintain dominance and support tumor cell survival even under adverse conditions that are oftentimes present in tumor tissue (low levels of oxygen, low glucose levels); under these conditions, the components shown in the right box are either not present or are only weakly active. However, when the tumor cell encounters additional ER stress, such as through the pharmacologic inhibition of SERCA, the already present low-level ER stress will be greatly aggravated and the components shown in the right box become activated and gain dominance; under these conditions, the defensive effort of components in the left box is being overwhelmed, and the components in the right box will execute tumor cell death. Note that the listed caspase 12 refers to the murine form of this enzyme; the human orthologue is caspase 4 (i.e., human caspase 4 and mouse caspase 12 execute similar functions during the events of the ESR).

FIG. 1 illustrates a simplified model of ER stress response. In this figure, top-to-bottom alignment corresponds to the duration of stress (9). The different signaling events are grouped left-to-right according to whether they have a pro-apoptotic (apoptosis) or anti-apoptotic (survival) effect on the cell. The scale at the bottom of the figure signifies the intricate balance between these two types of signals. In an early phase of the stress response, translational attenuation occurs to reduce the load of ER stress. In the next phase, several groups of genes are transcriptionally induced for long-term adaptation to ER stress. New synthesis of stress-induced proteins escapes from the general translational attenuation. To cope with the unfolded proteins in the ER, ER chaperones are first induced to refold them and if this response is inadequate, ER associated degradation (ERAD) components are then induced to eliminate the unfolded proteins. To remodel the ER, a variety of genes such as those of amino-acid import, glutathione biosynthesis, and oxidation protection are also induced. To elicit immune response and antiapoptotic effect, NFκB is activated. On the other hand, if severe ER stress conditions persist, the apoptosis signaling pathways are activated, including induction of CHOP and activation of c-Jun N-terminal kinase (JNK kinase) and caspase-12. The pivot point between survival or apoptosis may depend on the balance between survival signaling and apoptosis signaling.

Figure 2:
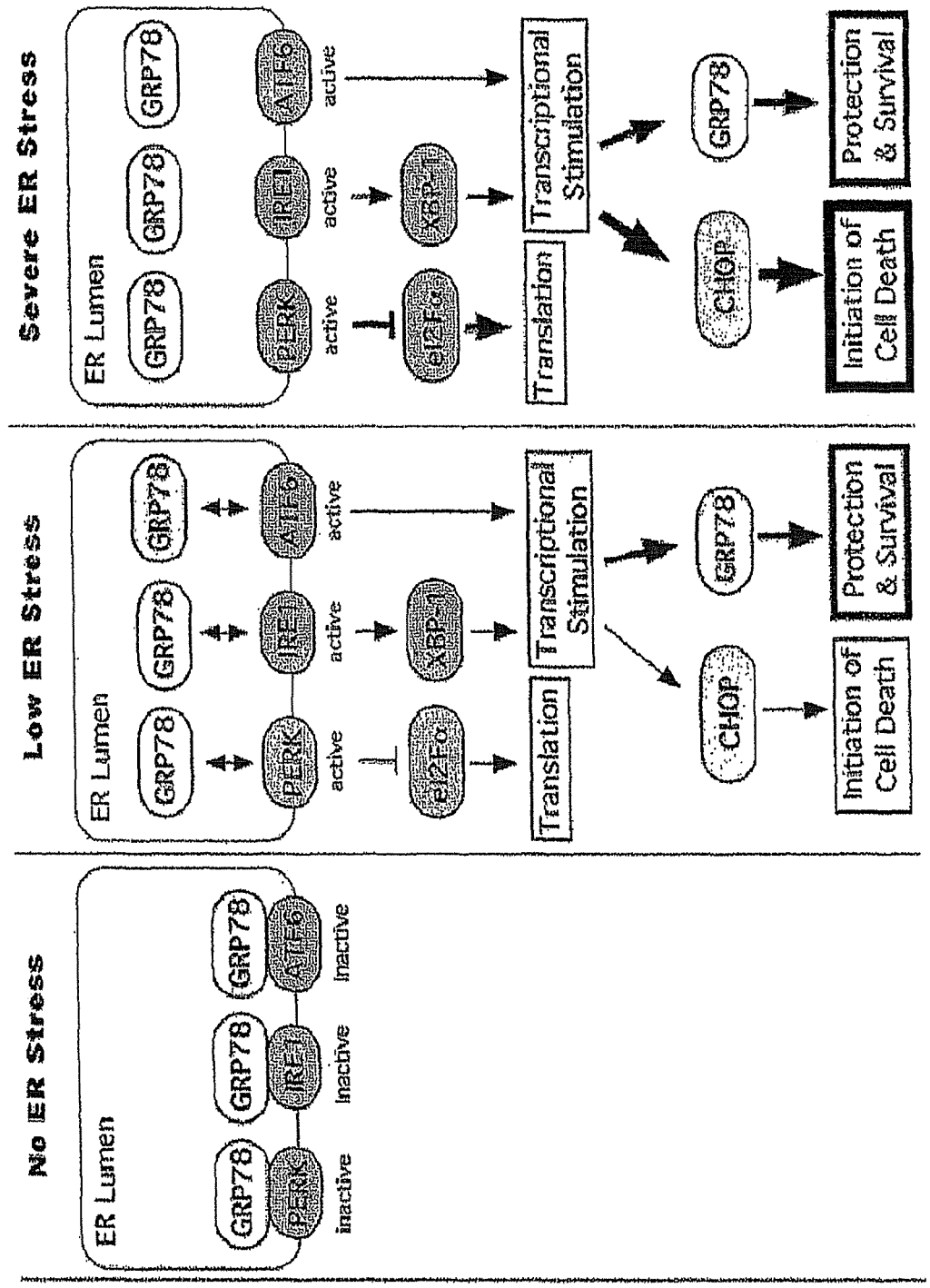
FIG. 2 illustrates the three major activity levels of the ER stress response system and the antagonistic defensive/pro-apoptotic functions of GRP78 and CHOP: (A) The "No ER Stress" condition (left) is the default situation in normal cells. Here, very low levels of GRP78 in the ER lumen bind to PERK, IRE1, and ATF6, and keep these ER stress components in their inactive states. (B) In cancer cells, chronic stress (low glucose, hypoxia, misfolded proteins) generates the "Low ER Stress" condition (middle). Here, low levels of continuous stress lead to the partial activation of the ER stress response system, with emphasis on elevated levels of GRP78 (thickened arrows), which provide the protective component of the ER stress system and furthermore increase chemo-resistance of tumor cells. In this scenario, the ER transmembrane components PERK, IRE1, and ATF6 display low levels of activity, which presumable are fine-tuned and adjusted by GRP78. Elevated levels of GRP78 help to neutralize deleterious effects of the initial stress condition, such as through the ability to act as a chaperone for misfolded proteins. (C) Persistent, high level stress generates the "Severe ER Stress" situation (right), which is characterized by severe (but transient) inhibition of protein synthesis via PERK-mediated phosphorylation (=inactivation) of translation initiation factor 2 alpha (eIF2α) (thick lines). Under these conditions, the protective effort of GRP78 is overwhelmed, and the activation of pro-apoptotic CHOP and subsequent initiation of cell death dominates (very thick arrows). Our work has demonstrated that during treatment of tumor cells with DMC, the "Severe ER Stress" scenario applies. In the continuous presence of this drug, the cell is unable to neutralize drug-induced stress, despite elevated levels of GRP78; instead, strong induction of CHOP and activation of caspase 4 initiate apoptosis, and the cell dies.

FIG. 2 illustrates the three conditions of ER stress, i.e. no ER stress, low ER stress and severe ER stress. The present invention describes methods, compounds and compositions which are capable of inducing apoptosis in those cells that are in a state of low level ER stress but are otherwise able to survive. The provided compounds "nudge" such cells with low ER stress towards a severe ER stress condition that pivots the signaling balance of the cell away from survivable conditions and towards apoptosis. The ability of the provided compounds to simply aggravate ER stress allows their use in this manner even if they exhibit only moderate pro-apoptotic potency, which also minimizes the induction of apoptosis in normal cells that typically exist under conditions of no ER stress. Under typical low ER stress conditions GRP78 is expressed in the cells at levels that are typically greater than two times its occurrence in normal cells while the corresponding levels of CHOP are not sufficient to initiate apoptosis. However, upon the use of compounds and compositions provided by this invention, the levels of CHOP are increased to levels sufficient to overcome the protective effects of the corresponding levels of GRP78, resulting in a condition of severe stress and the initiation of apoptosis. In essence the provided compounds, rather than being able to initiate ER stress and induce apoptosis in any type of cells, simply serve as "the straw that breaks the camel's back" by aggravating the ER stress of cells that are already in low ER stress. This key feature of the provided compounds enables their ability to serve as well-tolerated potential therapeutic agents for a variety of conditions whose pathogenesis involves cells in a state of low ER stress that can benefit from the induction of apoptosis in such cells. This situation exists in many forms of cancer as well as several other diseases.

ER Stress Response and Cancer Therapy

Although the relevance of ER stress to tumor growth and survival has begun to be recognized, very little is known with regards to its potential exploitation for purposes of tumor therapy. More importantly, there are yet no known points of attack in the ER stress response pathway or compounds that may provide a basis for viable therapeutic regimens.

For example, one potentially effective mode of triggering ER stress response is the inhibition of the sarcoplasmic/ endoplasmic reticulum $Ca^{2+}$-ATPase (SERCA), an intracellular membrane bound enzyme which sequesters cytosolic $Ca^{2+}$ into its intracellular ER storage compartment. Inhibition of SERCA leads to the release of $Ca^{2+}$ into the cytoplasm and resulting in activation of severe ER stress, leading to apoptosis. Although several inhibitors of SERCA have been described, none of these has an acceptable therapeutic profile to be used as a proapoptotic agent for cancer therapy. For instance, the most potent SERCA inhibitor, the natural product thapsigargin, is not suitable as a therapeutic agent due to its high toxicity and its histamine-release ability.

Another compound that was found to be a SERCA inhibitor is the anti-inflammatory drug celecoxib (Celebrex®) which is an inhibitor of cyclooxygenases-2 (COX-2) (Dannenberg, A J and Subbaramaiah, K, Cancer Cell 2003: 4:431). However, long-term use of COX-2 inhibitors has been linked to potentially life-threatening cardiovascular risks, that resulted in the withdrawal of the drug rofecoxib (Vioxx®) (Funk, C D and Fitzgerald, G A, Journal of Cardiovascular Pharmacology 2007; 50:470). Moreover, it is generally believed that the biochemical mechanism underlying the anticancer activities of COX-2 inhibitors (coxibs) and other NSAIDs are through the inhibition of cyclooxygenase (COX) enzymes, which catalyze the initial step in prostaglandin synthesis (10). The fact that celecoxib is a member of the COX-2 specific inhibitors known as coxibs leaves open the possibility that its anticancer activity can be also linked to COX-2 inhibition.

In several recent studies, it has been noted that treatment of cultured cells with various NSAIDs, including celecoxib, generated increased levels of intracellular calcium ($[Ca^{2+}]_i$) with subsequent activation of the ER stress response (ref. 11-16). Although these observations hint at the possibility that NSAID, as a class, may induce apoptosis through the ER stress response pathway, the high level of NSAIDs concentration (0.1 to >1.0 mmol/L) needed to elicit this effect makes such casual connection highly speculative. At these concentrations, other effects of NSAIDs such as COX-2 inhibition will likely dominate, rendering them unlikely candidates as a tool for inducing apoptosis with high specificity.

Surprisingly, in a series of reports, it was found that celecoxib can still exert potent anti-proliferative and pro-apoptotic effects in the absence of any apparent involvement of COX-2 (ref. 17-23). While these observations suggest that celecoxib may have a secondary target independent of COX-2 which leads to apoptosis in the cancerous cells, the underlying mechanism was not understood.

The inventors of the present invention have undertaken experiments to study this unknown mechanism and have unexpectedly discovered that the COX-2 independent antitumor activity of celecoxib is in fact through the ER stress response pathway. Moreover, it was found that there exist structural analogues of celecoxib which exhibit potent activity in inducing ER stress, both in vitro and in vivo (see EXAMPLES for supporting experiments and data). Although NSAIDs are known to be able to stimulate ER stress response at high concentrations and triggering the expression of both the prosurvival GRP78 and the proapoptotic CHOP proteins, apparently, the effect of celecoxib resulted in intense ER stress which led to elevated CHOP expression that overwhelmed the protective effect of GRP78, which in turn activated caspase-4 and committed the cell to apoptosis.

DEFINITIONS

As used herein, the phrase "ER stress" collectively refers to the various physiological and pathological conditions that may impair protein synthesis in the ER.

As used herein, the term "SERCA" is an acronym for Sarcoplasmic/Endoplasmic Reticulum $Ca^{2+}$-ATPase, which is a small family of highly conserved proteins (isoforms), all of which function as calcium transmembrane pumps in a similar manner.

As used herein, the term "COX-2" refers to cyclooxygenase-2, also known as prostaglandin-endoperoxidase 2 (prostaglandin G/H synthase and cyclooxygenase)

As used herein, the term "CHOP" refers to CCAAT/ enhancer binding protein homologous transcription factor, also called growth arrest and DNA damage-inducible gene 153 (GADD153)

As used herein, the phrase "ER-stress aggravating agent" refers to an agent that is capable of inducing or aggravating a stress in ER, whether directly or indirectly. The constitution of such an agent is not particularly limited, and may be chemical or physical in nature. Exemplary physical agents may include temperature, radiation, and sound, but not limited thereto. Exemplary chemical agents may include cellular signaling molecules, cytotoxic agents, toxins, or other metabolites, but not limited thereto In addition, specific conditions of the cellular microenvironment, such as hypoxia, low pH, shortage of nutrients, may trigger ER stress.

As used herein, the term "prodrug" refers to a pharmacological substance (drug) where the parent molecule is either inactive or minimal activity.

As used herein, the term "synergy" or "synergistic effect" refer to drug combinations where the resultant pharmacologic effect is greater than two times the activity compare with the activity of the drugs used individually (i.e. the combination is greater than the sum of its parts).

As used herein, the nomenclature alkyl, alkoxy, carbonyl, etc. is used as is generally understood by those of skill in this art.

As used in this specification, alkyl groups can include straight-chained, branched and cyclic alkyl radicals containing up to about 20 carbons, or 1 to 16 carbons, and are straight or branched. Exemplary alkyl groups herein include, but are not limited to, methyl, ethyl, propyl, isopropyl, isobutyl, n-butyl, sec-butyl, tert-butyl, isopentyl, neopentyl, tert-pentyl and isohexyl. As used herein, lower alkyl refer to carbon chains having from about 1 or about 2 carbons up to about 6 carbons. Suitable alkyl groups may be saturated or unsaturated. Further, an alkyl may also be substituted one or more times on one or more carbons with substituents selected from a group consisting of C1-C15 alkyl, allyl, allenyl, alkenyl, C3-C7 heterocycle, aryl, halo, hydroxy, amino, cyano, oxo, thio, alkoxy, formyl, carboxy, carboxamido, phosphoryl, phosphonate, phosphonamido, sulfonyl, alkylsulfonate, arylsulfonate, and sulfonamide. Additionally, an alkyl group may contain up to 10 heteroatoms, in certain embodiments, 1, 2, 3, 4, 5, 6, 7, 8 or 9 heteroatom substituents. Suitable heteroatoms include nitrogen, oxygen, sulfur and phosphorous.

As used herein, "cycloalkyl" refers to a mono- or multi-cyclic ring system, in certain embodiments of 3 to 10 carbon atoms, in other embodiments of 3 to 6 carbon atoms. The ring systems of the cycloalkyl group may be composed of one ring or two or more rings which may be joined together in a fused, bridged or spiro-connected fashion.

As used herein, "aryl" refers to aromatic monocyclic or multicyclic groups containing from 3 to 16 carbon atoms. As used in this specification, aryl groups are aryl radicals which may contain up to 10 heteroatoms, in certain embodiments, 1, 2, 3 or 4 heteroatoms. An aryl group may also be optionally substituted one or more times, in certain embodiments, 1 to 3 or 4 times with an aryl group or a lower alkyl group and it may be also fused to other aryl or cycloalkyl rings. Suitable aryl groups include, for example, phenyl, naphthyl, tolyl, imidazolyl, pyridyl, pyrroyl, thienyl, pyrimidyl, thiazolyl and furyl groups.

As used in this specification, a ring is defined as having up to 20 atoms that may include one or more nitrogen, oxygen, sulfur or phosphorous atoms, provided that the ring can have one or more substituents selected from the group consisting of hydrogen, alkyl, allyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, phosphonate, phosphonamido, and sulfonyl, and further provided that the ring may also contain one or more fused rings, including carbocyclic, heterocyclic, aryl or heteroaryl rings.

As used herein, alkenyl and alkynyl carbon chains, if not specified, contain from 2 to 20 carbons, or 2 to 16 carbons, and are straight or branched. Alkenyl carbon chains of from 2 to 20 carbons, in certain embodiments, contain 1 to 8 double bonds, and the alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrrolidinyl, pyrimidinyl, tetrazolyl, thienyl, pyridyl, pyrrolyl, N-methylpyrrolyl, quinolinyl and isoquinolinyl.

As used herein, "heterocyclyl" refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, or the nitrogen may be quaternized to form an ammonium group where the substituents are selected as above.

EXEMPLARY EMBODIMENTS OF THE PRESENT INVENTION

1. Methods for Inducing or Aggravating Stress in a Cell's ER to Trigger Apoptosis In a first aspect, the present invention provides a method of inducing or aggravating stress in a cell's endoplasmic reticulum (ER) to trigger apoptosis.

As set forth above, methods according to this aspect of the present invention are based on the discovery that by inducing or aggravating ER for a sufficient intensity and duration, the proapoptotic effect of the elevated expression of CHOP will overtake the protective effect of GRP78, leading to activation of a caspase such as caspase 4 and/or caspase 7, thereby, committing the cell to apoptosis. It is also based on the discovery that there exist agents capable of specifically inducing or aggravating ER stress in a selected cell without causing concomitant side-effects in other non-targeted cells.

Specifically, preferred embodiments in accordance with this aspect of the present invention generally comprise the steps of 1). inhibiting SERCA activity selectively in said cell without inhibiting COX-2 activity; and 2). elevating the expression of CHOP in said cell, wherein, the combination of inhibiting SERCA activity and elevating CHOP expression results in a condition favorable for initiation of apoptosis in the cell.

It is envisioned that aggravation of ER stress via the inhibition of SERCA can be achieved with any suitable agent known in the art or future identified agents that are developed to inhibit SERCA and induce apoptosis.

Preferably, the specificity of the agent is such that it does not inhibit COX-2 activity or trigger the release of histamine.

In a preferred embodiment, selective inhibition of SERCA activity is accomplished by administering a pharmaceutically effective amount of an ER-stress aggravating agent capable of selectively inhibiting SERCA, directly or indirectly, for a duration sufficient to elevate cytoplasmic calcium concentration significantly above normal level so as to cause apoptosis. In this embodiment, elevation of CHOP expression may be co-effected as a result of the aggravated ER-stress, or may be specifically induced by a CHOP expression enhancer/inducer. Exemplary CHOP expression enhancer/inducer may include transfection of plasmid-based constructs or infection with viral expression constructs, but is not limited thereto.

1.1 Embodiments in which the ER-Stress Aggravating Agent is a Compound or a Pharmaceutical Composition In some preferred embodiments, the ER-stress aggravating agent is a compound or a pharmaceutical composition containing the compound, wherein the compound is one having the general formula:

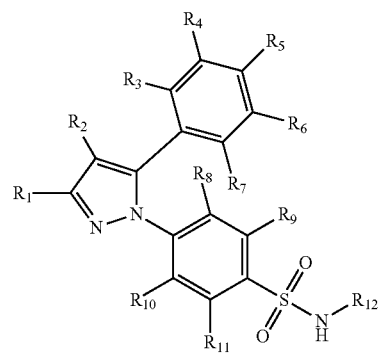

and wherein:

$R_1$ is methyl, fluoromethyl, difluoromethyl, trifluoromethyl, alkyl, fluoroalkyl, difluoroalkyl, trifluoroalkyl, polyfluoroalkyl, hydroxyalkyl, or carboxyalkyl;

$R_2$ is hydrogen, fluoro, chloro, bromo; fluoromethyl, difluoromethyl, trifluoromethyl, alkyl, fluoroalkyl, difluoroalkyl, trifluoroalkyl, polyfluoroalkyl, hydroxyalkyl, or carboxyalkyl;

$R_3$-$R_7$ are independently selected from a group consisting of: hydrogen, fluoro, chloro, bromo, alloxy, alkyl, fluoroalkyl, difluoroalkyl, trifluoroalkyl, polyfluoroalkyl, hydroxyalkyl, or carboxyalkyl, aryl and heteroaryl;

$R_8$-$R_{11}$ are independently selected from a group consisting of: hydrogen, fluoro, chloro, bromo; fluoromethyl, difluoromethyl, trifluoromethyl, alkyl, fluoroalkyl, difluoroalkyl, trifluoroalkyl, polyfluoroalkyl, hydroxyalkyl, carboxyalkyl, alkenyl, alkynyl, cycloalkyl, heterocyclic, aryl, or heteroaryl; and $R_{12}$ is hydrogen, acetyl, acyl, alkyl, fluoroalkyl, difluoroalkyl, trifluoroalkyl, polyfluoroalkyl, hydroxyalkyl, carboxyalkyl; aminoacyl, aminoalkyl, cycloalkyl, heterocyclic, aryl, or heteroaryl.

In some more preferred embodiments, $R_1$ is trifluoromethyl.

In other preferred embodiments, $R_2$, $R_8$-$R_{12}$ are hydrogen, or $R_4$, $R_5$ and $R_7$ are hydrogen. In one embodiment, $R_1$ is trifluoromethyl and $R_2$, $R_4$, $R_5$, $R_7$-$R_{12}$ are all hydrogen.

In another preferred embodiment, the aggravating agent is 4-[5-(2,5-dimethylphenyl)-3-(trifluoromethyl)-1H-pyrazol-1-yl]benzenesulfonamide, 4-[5-(2,5-di(trifluoromethyl)phenyl)-3-(trifluoromethyl)-1H-pyrazol-1-yl]benzenesulfonamide, 4-[5-(2,5-dibromophenyl)-3-(trifluoromethyl)-1H-pyrazol-1-yl]benzenesulfonamide, or an analogue thereof.

For compounds that contain at least one fluorine-containing functional group, such as a CF3 group, the provided compounds can enable the monitoring and imaging of their in vivo actions by using magnetic resonance imaging. This can be a very valuable feature for difficult to treat and difficult to monitor diseases such as brain cancer.

1.2 Embodiments in which the Aggravating Agent is a Prodrug

As set forth above, the present invention also includes those embodiments in which either directly or indirectly inhibits SERCA and thus aggravating ER stress. In one exemplary embodiment, the aggravating agent is a prodrug which can be converted into an active compound able to inhibit SERCA via metabolism or other conversion means. For example, in those embodiments where the aggravating agent is a recombinant molecule, a translocation peptide may be attached to allow the agent to translocate across the membrane. In other embodiments the provided compounds contain functional groups that upon metabolic oxidation, proteolytic cleavage or hydrolysis convert the provided compound into an active ER aggravating agent. Those skilled in the art can recognize that such functional groups include but are not limited to methyl or alkyl groups, ester groups, carbonate groups, amide groups, peptides, or their cyclic or polymeric derivatives.

1.3 Embodiments in which a Combination of Aggravating Agent is Used

Methods in accordance with some embodiments of the present invention may further include a step of applying an additional one or more ER-stress aggravating agent. Preferably, this additional one or more ER-stress aggravating agent acts through a different stress-inducing mechanism.

It is another unexpected discovery of the present invention that when different strategies of aggravating ER-stress are used in combination, a synergistic effect may be achieved.

For example, in one embodiment, when the drug bortezomib (which induces apoptosis through inhibition of proteasome 26S) is used together with celecoxib, the level of ER-stress was elevated and the rate of apoptosis was significantly increased (see Example 2).

Accordingly, it is envisioned that any of the apoptosis induction strategies listed in Table 1 may be advantageously combined with strategies of the present invention (i.e. induction of apoptosis through ER-stress aggravation) to achieve a synergistic effect in inducing apoptosis.

In some preferred embodiments, a first ER-stress aggravating agent capable of selectively inhibiting SERCA activity without inhibiting COX-2 or triggering histamine release may be combined with a second ER-stress aggravating agent which is capable of increasing the concentration of misfolded or damaged protein in the ER. Exemplary agents suitable for use as the second ER-stress aggravating agent may include a proteasome inhibitor (e.g. bortezomib, or an analogue thereof), or a protease inhibitor (e.g. nelfinavir, atazanavir, fosamprenavir, ritonavir, indinavir, or an analogue thereof).

1.4 Embodiments in which an Apoptosis Enhancer is Used

In some further embodiments of the present invention, the ER-stress aggravating agent may be assisted by further applying an apoptosis enhancer to the cell. In the context of the present invention, an apoptosis enhancer is one that amplifies the effect of ER-stress in relation to the induction of apoptosis. Preferably, an apoptosis enhancer is a chemical or biological agent that is capable of upregulating the expression of CHOP, overcoming the protective effect of GRP78, and activating a caspase such as caspase-4 and/or caspase-7. Exemplary apoptosis enhancer may include a siRNA for GRP78 or an inhibitor of GRP78 function, but not limited thereto. Additionally, apoptosis enhancers may also be synthetic or natural compounds, including, but not limited to, BH3-mimetics that block the activity of anti-apoptotic proteins of the Bcl-2 family, such as ABT-737.

2. Method for Screening, Selecting, or Designing Compounds Useful as an ER-Stress Aggravating Agent In a second aspect, the present invention provides a method for screening, selecting, or designing compounds useful for inducing or aggravating ER stress in a cell to trigger apoptosis in the cell.

Embodiments according to this aspect of the present invention have the general steps of: 1). Obtaining information about a test compound; 2). Identifying the test compound as a potential ER-stress agent if the test compound is an inhibitor of SERCA and is not an inhibitor of COX-2. Preferably, the identified compound also does not trigger the release of histamine. In the obtaining step, information about the test compound to be obtained may include SERCA inhibitory activity of the compound, COX-2 inhibitory activity of the compound, and histamine release activity of the compound.

The evidence of ER stress in a cell can be determined by the presence of high levels of GRP78 that occur at levels greater than twice the GRP78 levels in normal tissues. The levels of GRP78 can be determined by those skilled in the art using common techniques, such as those described in the examples.

Source of the test compound may come from any common source known in the art, including commercial chemical vendors, chemical libraries generated by combinatorial chemistry, or modified analogues of known SERCA inhibitors, but are not limited thereto.

In the case where the desired information about a test compound is not already known or otherwise available, the step of obtaining information may involve performing assays to characterize the test compounds. In such cases, any assays commonly known in the art may be used, including chemical assays and cell-based assays, but not limited thereto. Preferably, the assays chosen should yield quantifiable results easily comparable to other test compounds.

Because screening of new compounds is necessarily a trial-and-error process and the steps of obtaining information, identifying the promising candidate compounds from the test compounds are repeated for each test compound.

In some preferred embodiments, a large number of test compounds are used and the steps of obtaining, identifying, and repeating are performed in a high-throughput format. General principles of high-throughput drug screening are well-known in the art (for a recent review, see Walters et al., Nat Rev Drug Discov. 2003 April; 2(4):259-66, the content of which is incorporated herein by reference).

In addition to screening existing chemical sources, once a sufficient number of compounds have been tested and identified, computational analysis may also be employed to further optimize or generate new candidate compounds suitable for use as an ER-stress aggravating agent. Any commonly known computational drug discovery methods may be advantageously adapted for this task. Preferably, ligand-based methodologies are used. (for a recent review on ligand-based drug design, see Bacilieri et al., Current Drug Discovery Technologies, Volume 3, Number 3, September 2006, pp. 155-165(11), the content of which is incorporated herein by reference).

In a preferred embodiment, a quantitative structure-activity relationship (QSAR) analysis is performed (for a review on adaptation and incorporation of computational methodologies with high-throughput screening, see Davies et al., Curr Opin Chem Biol. 2006 August; 10(4):343-51. Epub 2006 Jul. 5, the content of which is incorporated wherein by reference).

3. Compounds Useful as an ER-Stress Aggravating Agent

In a third aspect, the present invention also provides compounds useful as an ER stress aggravating agent, having the general formula:

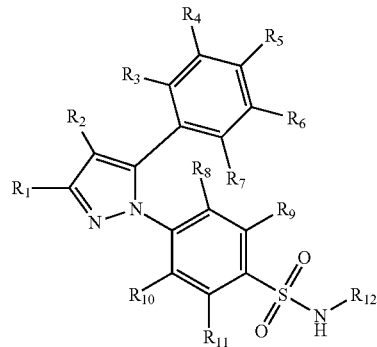

wherein,
$R_1$ is methyl, fluoromethyl, difluoromethyl, trifluoromethyl, alkyl, fluoroalkyl, difluoroalkyl, trifluoroalkyl, polyfluoroalkyl, hydroxyalkyl, or carboxyalkyl;

$R_2$ is hydrogen, fluoro, chloro, bromo; fluoromethyl, difluoromethyl, trifluoromethyl, alkyl, fluoroalkyl, difluoroalkyl, trifluoroalkyl, polyfluoroalkyl, hydroxyalkyl, or carboxyalkyl;

$R_3$-$R_7$ are independently selected from a group consisting of: hydrogen, fluoro, chloro, bromo, alloxy, alkyl, fluoroalkyl, difluoroalkyl, trifluoroalkyl, polyfluoroalkyl, hydroxyalkyl, or carboxyalkyl, aryl and heteroaryl;

$R_8$-$R_{11}$ are independently selected from a group consisting of: hydrogen, fluoro, chloro, bromo; fluoromethyl, difluoromethyl, trifluoromethyl, alkyl, fluoroalkyl, difluoroalkyl, trifluoroalkyl, polyfluoroalkyl, hydroxyalkyl, carboxyalkyl, alkenyl, alkynyl, cycloalkyl, heterocyclic, aryl, or heteroaryl; and $R_{12}$ is hydrogen, acetyl, acyl, alkyl, fluoroalkyl, difluoroalkyl, trifluoroalkyl, polyfluoroalkyl, hydroxyalkyl, carboxyalkyl; aminoacyl, aminoalkyl, cycloalkyl, heterocyclic, aryl, or heteroaryl.

Preferred embodiments are compounds wherein $R_1$ is trifluoromethyl, while other preferred embodiments are compounds wherein $R_2$, $R_8$ and $R_9$ are hydrogen or compounds wherein $R_4$, $R_5$, and $R_7$ are hydrogen, as well as compounds wherein $R_1$ is trifluoromethyl, and $R_2$, $R_4$, $R_5$, $R_7$, $R_8$ and $R_9$ are hydrogen.

Other preferred embodiments are compounds wherein $R_3$ and $R_6$ are selected from a group consisting of: hydrogen, fluoro, chloro, bromo; fluoromethyl, difluoromethyl, trifluoromethyl, alkyl, aryl, heteroaryl, fluoroalkyl, difluoroalkyl, trifluoroalkyl, polyfluoroalkyl, hydroxyalkyl, or carboxyalkyl.

An example of preferred embodiments are compounds that are structural analogs of 4-[5-(2,5-dimethylphenyl)-3-(trifluoromethyl)-1H-pyrazol-1-yl]benzenesulfonamide such as: 4-[5-(2,5-di(trifluoromethyl)phenyl)-3-(trifluoromethyl)-1H-pyrazol-1-yl]benzenesulfonamide and 4-[5-(2,5-dibromophenyl)-3-(trifluoromethyl)-1H-pyrazol-1-yl]benzenesulfonamide.

Referring to FIG. 19, two exemplary compounds in accordance with the present invention have shown surprisingly potent cell killing effect compare to DMC. In the figure, DMC stands for 4-[5-(2,5-dimethylphenyl)-3-(trifluoromethyl)-1H-pyrazol-1-yl]benzenesulfonamide; DBrC stands for 4-[5-(2,5-dibromophenyl)-3-(trifluoromethyl)-1H-pyrazol-1-yl]benzenesulfonamide; and DTF3C stands for 4-[5-(2,5-ditrifluoromethylphenyl)-3-(trifluoromethyl)-1H-pyrazol-1-yl]benzenesulfonamide.

Another preferred embodiment, the compounds are prodrug compounds that can be converted in vivo to an ER-stress aggravating agent that can act as a SERCA inhibitor. Those in the art will recognize such compounds as having the general structure:

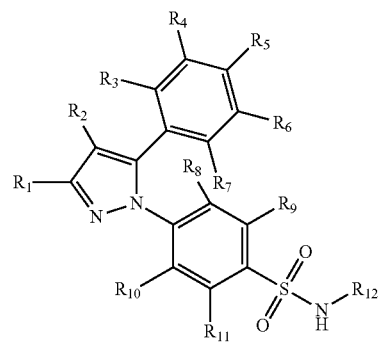

-continued

At least one group R₁-R₁₂

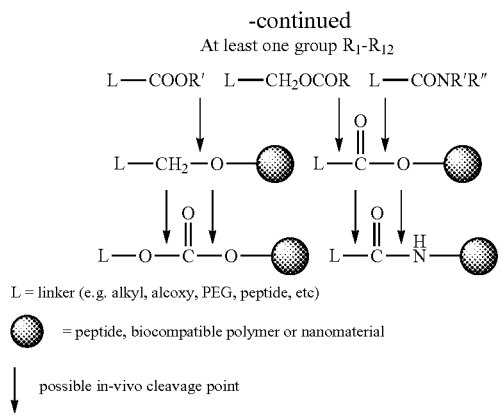

L = linker (e.g. alkyl, alcoxy, PEG, peptide, etc)

● = peptide, biocompatible polymer or nanomaterial

↓ possible in-vivo cleavage point wherein at least one group of $R_1$-$R_{12}$ has a side-chain selected from the linker groups shown above.

4. Pharmaceutical Compositions Useful as an ER-Stress Aggravating Agent

In a fourth aspect, the present invention also provides a pharmaceutical composition useful for inducing or aggravating ER stress in a cell to trigger apoptosis in the cell. Embodiments of the present invention generally include an ER-stress aggravating agent, and a pharmaceutically acceptable carrier.

Any chemical-based ER-stress aggravating agent described above may be suitably formulated to facilitate administration of the active ingredient. In a preferred embodiment, the ER-stress aggravating agent is a compound having the general formula also described in the first aspect above, or a pharmaceutically stable salt thereof.

For the carrier, any commonly known carrier that is compatible with the chosen active ingredient may be suitably used. Preferably, the carrier is one suitable for oral formulation.

5. Therapeutic Methods

In a fifth aspect, the present invention also provides a method for treating a diseased condition in a patient by inducing or aggravating ER stress in selected diseased cells to trigger apoptosis in the cells.

Embodiments according to this aspect of the present invention include the general steps of administering a pharmaceutically effective amount of a pharmaceutical composition according to the fourth aspect of the present invention described above. Any methods for inducing or aggravating ER stress according to embodiments set forth in the first aspect of the present invention may be suitably adapted for treatment methods of the present invention.

In a preferred embodiment, the diseased cells are in a state of ER stress prior to administration of the pharmaceutical composition.

The method of treatment described herein is a general method that is applicable to all forms of diseases whether in the pathogenesis include disregulation of apoptosis as a contributing mechanism. In preferred embodiments, cancer is the preferred disease for the treatment methods of the present invention. Exemplary cancers that may be applicable include glioblastoma multiforme, breast carcinoma, pancreatic carcinoma, Burkitt's lymphoma, multiple myeloma, neuroblastoma, prostate cancer, colorectal cancer, metastatic breast cancer, recurring cancer, and drug-resistant cancer, but are not limited thereto.

Another embodiment of the presence invention involves the treatment of chemoresistant tumors by inhibiting invasion, vasculogenesis, and angiogenesis. In chemoresistant tumor cells, the tumor vasculature is not responsive to many therapeutic drugs, including Temozolomide (TMZ), the agent most commonly used for glioblastoma multiforme (GBM) therapy. The tumor vasculature provides the nutrients, oxygen as well as the environment for tumor growth. Therefore agents that destroy these cells would be very useful in treating the residual or recurring tumors.

In yet another embodiment the present invention provides a method for the treatment of the perinecrotic rim of cancers, involving the induction of apoptosis via ER stress response modulation alone or in combination with conventional chemotherapy. More particularly, this invention can be employed for the treatment of especially difficult-to-treat cancers that do not respond well to chemotherapy, such as glioblastoma multiforme (GBM). Many cancers will outgrow their blood supply, where the consequence is the development of a necrotic center. The cancer cells at the "necrotic rim" are usually quiescent cells, exposed to an adverse microenvironment of low oxygenation, low pH, and low glucose. As consequence of this stressful environment, these cells have a high level of ESR. To thrive in this hostile environment, high resistance level of GRP78 is expressed to survive. These perinecrotic cancer cells are especially resistant to treatment by chemotherapy or radiation therapy, which typically target rapidly proliferating cells.

The present invention offers unique benefits for the treatment of brain tumors that are not possible with conventional chemotherapy. The blood brain barrier, although generally not intact at the blood-tumor interface, still impedes free access of chemotherapy to the tumor. Moreover, traditional cytotoxic chemotherapy targets rapidly proliferating cancer cells. GBM, however, is heterogeneous in nature. Pathologically, GBM is characterized by a necrotic center, a perinecrotic rim, and an invading vascularized periphery. This perinecrotic rim has been pathologically described as the pseudopalisades seen in pathological specimens in glioblastoma (Brat D J, et al, Cancer Res 2004, 64: 920-7). Chemotherapy and radiation traditionally target the well vascularized proliferating tumor cells in the interface of normal brain and tumor tissue. In contrast, the malignant cells in the perinecrotic rim of the brain tumor undergo less proliferation, and remain dormant, albeit with the potential to be activated. Once the proliferating tumor cells are killed by chemotherapy or radiation, the dormant glioblastoma cells in the perinecrotic zone begin to grow and invade again, repeating the process. This mechanism of dormant cell activation is very similar to the concept of trees growing in a rainforest. A rainforest has trees of varying height. If the tallest trees (similar to the well vascularized tumor region) are cut down, then the lower level trees (similar to the perinecrotic region cells) will grow up as they now receive the bulk of the sunlight. The end result is that the GBM recurs, with increased invasion into the normal brain. The glioblastoma cells in the perinecrotic zone have been previously characterized. They secrete increased levels of proteins in response to the low oxygen tension that is present in the perinecrotic zone, and angiogenesis factors. The perinecrotic cells proliferate significantly less and exhibit more cell death than the glioblastoma cells in the well vascularized periphery. Moreover, these tumor cells display increased migration, and increased secretion of specific enzymes associated with cell invasion (Brat D J, et al., Cancer Res 2004, 64: 920-7, the entire content of which is incorporated herein by reference).

Having generally described this invention, a further understanding can be obtained by reference to certain specific examples which are provided herein for purposes of illustration only and are not intended to be limiting unless otherwise specified.

EXAMPLES

Example 1

Calcium-Activated ER Stress as a Major Component of Tumor Cell Death Induced by 2,5-Dimethyl-Celecoxib (DMC), a Non-Coxib Analog of Celecoxib Materials and Methods
Materials Celecoxib is 4-[5-(4-methylphenyl)-3-(trifluoromethyl)-1H-pyrazol-1-yl]benzenesulfonamide (24). DMC is a close structural analogue, where the 5-aryl moiety has been altered by replacing 4-methylphenyl with 2,5-dimethylphenyl, resulting in 4-[5-(2,5-dimethylphenyl)-3-(trifluoromethyl)-1H-pyrazol-1-yl]benzenesulfonamide (20, 19). Both compounds were synthesized in our laboratory according to previously published procedures (see ref. 24 for celecoxib and ref. 19 for DMC). Each drug was dissolved in DMSO at 100 mmol/L (stock solution). For valdecoxib (25) and rofecoxib (26), commercial caplets of Bextra (Pfizer, New York, N.Y.) and Vioxx (Merck, Whitehouse Station, N.J.), respectively, were suspended in $H_2O$ to disintegrate the excipient, and the active ingredient was dissolved in DMSO at 25 mmol/L. In addition, we used pure rofecoxib powder that was synthesized in our laboratory according to established procedures (27). All traditional NSAIDs were purchased from Sigma (St. Louis, Mo.) in powdered form and dissolved in DMSO at 100 mmol/L. Thapsigargin and BAPTA-AM were obtained from Sigma and dissolved in DMSO. All drugs were added to the cell culture medium in a manner that kept the final concentration of solvent (DMSO)<0.5%.

Cell Lines and Culture Conditions

Most cell lines were obtained from the American Type Culture Collection (Manassas, Va.) and were propagated in DMEM or RPMI 1640 (Life Technologies, Grand Island, N.Y.) supplemented with 10% fetal bovine serum, 100 units/mL penicillin, and 0.1 mg/mL streptomycin in a humidified incubator at 37° C. and a 5% $CO_2$ atmosphere. The glioblastoma cell lines U251 and LN229 were provided by Frank B. Furnari and Webster K. Cavenee (Ludwig Institute of Cancer Research, La Jolla, Calif.).

Immunoblots and Antibodies

Total cell lysates were prepared by lysis of cells with radioimmunoprecipitation assay buffer (28), and protein concentrations were determined using the bicinchoninic acid protein assay reagent (Pierce, Rockford, Ill.). For Western blot analysis, 50 Ag of each sample were processed as described (29). The primary antibodies were purchased from Cell Signaling Technologies (Beverly, Mass.), Cayman Chemical (Ann Arbor, Mich.), or Santa Cruz Biotechnology, Inc. (Santa Cruz, Calif.) and used according to the manufacturer's recommendations. The secondary antibodies were coupled to horseradish peroxidase and detected by chemiluminescence using the SuperSignal West substrate from Pierce. All immunoblots were repeated at least once to confirm the results.

Immunohistochemistry

Immunohistochemical analysis of protein expression in tumor tissues was done with the use of the Vectastain avidin-biotin complex method kit (Vector Laboratories, Burlingame, Calif.) according to the manufacturer's instructions. This procedure uses biotinylated secondary antibodies and a preformed avidin: biotinylated enzyme complex that has been termed the avidin-biotin complex method technique. As the primary antibody, we used anti-CHOP antibody (Santa Cruz Biotechnology) diluted 1:100 in 2% normal goat blocking serum.

Apoptosis Measurements

Apoptosis in tumor sections was measured quantitatively with the use of the terminal deoxynucleotidyl transferase-mediated dUTP nick end labeling assay (30). All components for this procedure were from the ApopTag In situ Apoptosis Detection kit (Chemicon, Temecula, Calif.), which was used according to the manufacturer's instructions.

Apoptosis in cell cultures in vitro was determined by using the Cell Death Detection ELISA kit (Roche Diagnostics, Indianapolis, Ind.) according to the manufacturer's instructions. This immunoassay specifically detects the histone region (H1, H2A, H2B, H3, and H4) of mononucleosomes and oligonucleosomes that are released during apoptosis. Ninety-six-well plates were seeded with 1,000 cells per well and read at 405 nm in a Microplate Autoreader (Model EL 311 SX; Bio-Tek Instruments, Inc., Winooski, Vt.).

Colony Formation Assay

Twenty-four hours after transfection with small interfering RNA (siRNA), the cells were seeded into six-well plates at 200 cells per well. After complete cell adherence, the cells were exposed to drug treatment for 48 h. Thereafter, the drug was removed, fresh growth medium was added, and the cells were kept in culture undisturbed for 12 to 14 days, during which time the surviving cells spawned a colony of proliferating cells. Colonies were visualized by staining for 4 h with 1% methylene blue (in methanol) and then counted.

Transfections with SiRNA

Cells were transfected in six-well plates with the use of LipofectAMINE 2000 (Invitrogen, Carlsbad, Calif.) according to the manufacturer's instructions. The different siRNAs were synthesized at the microchemical core laboratory of the University of Southern California/K. Norris Jr. Comprehensive Cancer Center, and their sequences were as follows: siRNA targeted at green fluorescent protein (si-GFP),

```
                                   (SEQ ID NO: 1)
5'-CAAGCUGACCCUGAAGUUCTT-3' (sense)
and (SEQ ID NO: 2)
5'-GAACUUCAGGGUCAGCUUGTT-3' (antisense);

si-GRP78,
                                   (SEQ ID NO: 3)
5'-GGAGCGCAUUGAUACUAGATT-3' (sense)
and (SEQ ID NO: 4)
5'-UCUAGUAUCAAUGCGCUCCTT-3' (antisense);
and si-caspase-4,
```

```
                                               (SEQ ID NO: 5)
5'-AAGUGGCCUCUUCACAGUCAUTT-3'   (sense)
and
                                               (SEQ ID NO: 6)
5'-AAAUGACUGUGAAGAGGCCACTT-3'   (antisense).
```

Cytoplasmic Calcium Imaging

The cells were loaded by incubating them with 4 μmon Fura-2/AM (Invitrogen) for 30 min at room temperature in external solution containing 138 mmol/L NaCl, 5.6 mmol/L KCl, 1.2 mmol/L $MgCl_2$, 2.6 mmol/L $CaCl_2$, 10 mmol/L HEPES, and 4 mmol/L glucose (pH 7.4). After loading, the cells were rinsed and transferred to the imaging setup. The cells were treated with individual drugs for 10 s, whereas fluorescence was elicited with the excitation wavelength alternating between 350 and 380 nm, using a Polychromator V (TILL Photonics GmbH, Grafelfing, Germany) to provide illumination via a Zeiss Axiovert 100 microscope with a Zeiss Fluar 40 oil objective (Carl Zeiss, Jena, Germany). Images were captured using a Cascade 512B CCD camera (Photometrics, Tucson, Ariz.) controlled with MetaFluor software (Molecular Devices, Sunnyvale, Calif.) at 0.5 Hz acquisition frequency. Ratios of the images obtained at 350 and 380 nm excitation were used to show changes in the cytoplasmic calcium concentration, according to the principles developed by Grynkiewicz et al. (31).

Drug Treatment of Nude Mice

Four- to 6-week-old male athymic nu/nu mice were obtained from Harlan (Indianapolis, Ind.) and implanted s.c. with $5\times10^5$ U87 glioblastoma cells as described in detail elsewhere (32). For the determination of tumor growth during continuous drug treatment for several weeks, DMC or rofecoxib was mixed with the daily chow (150 g/kg for DMC; 40 mg/kg for rofecoxib), and tumor growth was monitored and recorded as described (32). For the analysis of short-term effects of drugs on CHOP expression and tumor cell death in vivo, as well as for the determination of drug concentrations in plasma and tumor tissue, tumorbearing animals were treated with 30, 90, 150, or 180 mg/kg of drug per day for 50 h; each animal received one half of the daily dose of the respective drug every 12 h via direct administration into the stomach with a stainless steel ballhead feeding needle (Popper and Sons, Inc., New Hyde Park, N.Y.). All animals were sacrificed 2 h after the final application of drug, and tumors and blood were collected for analysis. In all experiments, the animals were closely monitored with regard to body weight, food consumption, and clinical signs of toxicity; no differences between nondrug-treated control animals and drug-treated animals were detected.

Extraction of Plasma for Liquid Chromatography Mass Spectrometry Analysis

Blood was collected in heparinized syringes using cardiac puncture of nude mice. The blood was allowed to settle at room temperature for 30 min followed by centrifugation at 2,000 rpm for 5 min at 4° C. The plasma was separated from the cells and transferred to a fresh tube. To establish a standard reference, 25 μL of 1.0 μg/mL DMC or celecoxib were added to 50 μL plasma from untreated control animals. For the test samples, the same amount of DMC was added as an internal standard to plasma from animals that had been treated with celecoxib, whereas the same amount of celecoxib was added as an internal standard to plasma from animals that had been treated with DMC. After thorough vortexing, plasma proteins were precipitated using 425 μL acetonitrile and vortexing for 1 min. The entire mixture was centrifuged at 4,500 rpm for 5 min to separate the protein precipitate, and 400 μL of the supernatant were transferred to a fresh tube. The sample was evaporated using a steady stream of air, and the dried residue was reconstituted using 150 μL of mobile phase consisting of 80:20 (v/v) methanol:10 mmol/L ammonium acetate (pH 4.5). To remove any undissolved precipitates, the samples were again centrifuged at 4,500 rpm for 5 min, and the supernatant was transferred to a fresh tube. Ten microliters of each sample were analyzed in duplicate by liquid chromatography mass spectrometry.

To determine the amount of drug in each sample, an Agilent 1100 high-pressure liquid chromatography system (Agilent Technologies, Santa Clara, Calif.) coupled onto a Sciex API 3000 triple quadruple tandem mass spectrometer (Applied Biosystems, Foster City, Calif.) was used. To separate the analytes, a Thermo HyPURITY C18 column (50×4.6 mm, 3 micron; Thermo Fisher Scientific, Inc., Waltham, Mass.) was used. The mobile phase consisted of 80:20 (v/v) methanol:10 mmol/L ammonium acetate (pH 4.5). The flow rate to separate the analytes was 350 μL/min, where the retention time for DMC and celecoxib were 3.50 and 3.10 min, respectively. The analytes were then introduced into the Sciex API 3000, which was set in the negative ion mode. The level of DMC and celecoxib used the transition ions 394.0→330.2 and 380.0→316.2, respectively. The lower level of quantification of this assay was established at 5 ng/mL.

Results

Figure 3:
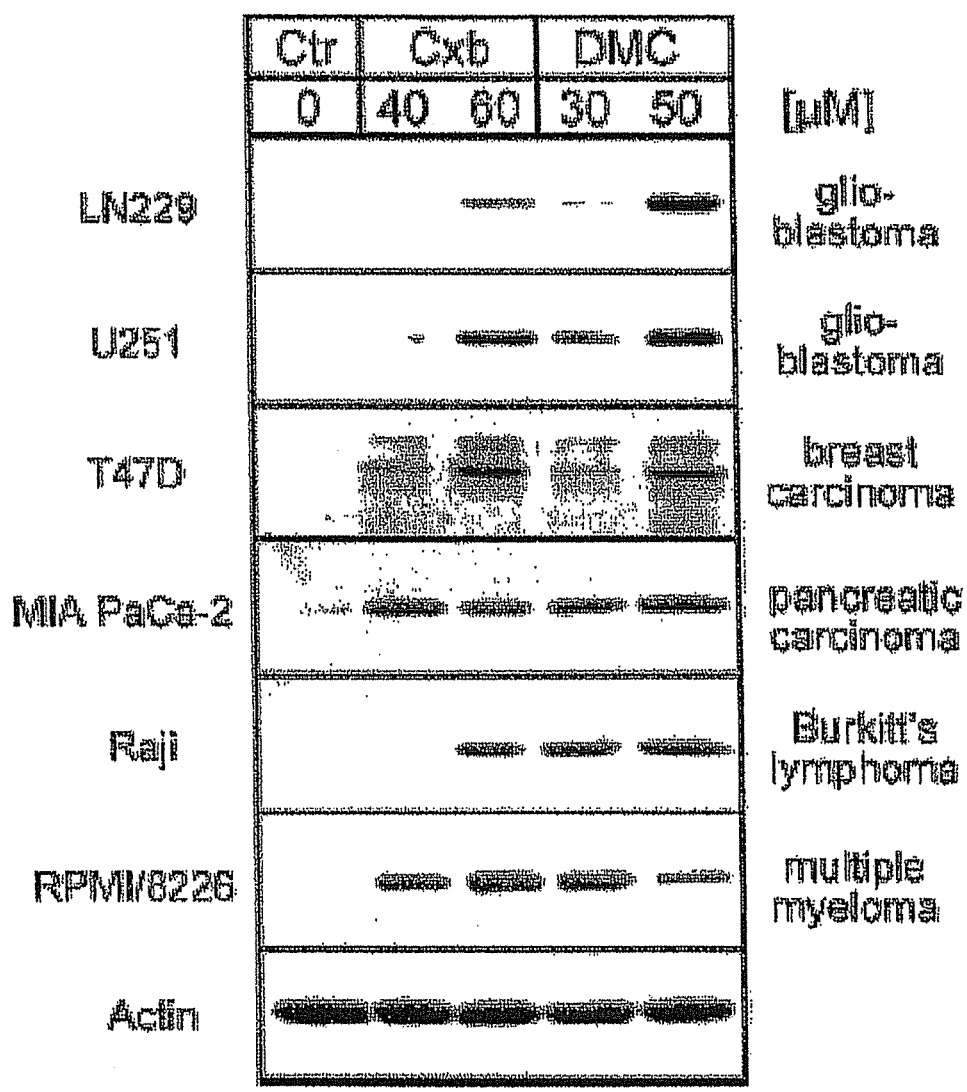
FIG. 3 shows that Celecoxib and DMC induce CHOP protein levels in various cancer cell lines. Several different cancer cell lines (as indicated on the left) were cultured in the presence of celecoxib (Cxb; 40 and 60 μM) or DMC (30 and 50 μM) for 48 hours (Co: control, non-treated cells).

DMC is a close structural analogue of celecoxib that lacks the ability to inhibit COX-2. To investigate whether this compound would be able to induce the ESR, we treated various tumor cell lines with DMC, or in parallel with celecoxib, and determined the expression level of CHOP protein. CHOP is a proapoptotic component of the ESR and is critically involved in the initiation of cell death after ER stress; therefore, we used it as a well-established indicator of ESR in our experimental system. As shown in FIG. 3, both DMC and celecoxib were able to potently induce CHOP in glioblastoma, breast carcinoma, pancreatic carcinoma, Burkitt's lymphoma, and multiple myeloma cell lines. Thus, both drugs seemed to stimulate the ESR, although celecoxib seemed to be somewhat less potent than DMC in glioblastoma and Burkitt's lymphoma cell lines.

To evaluate the extent of the ESR after DMC treatment, we analyzed additional indicators of the ESR and compared the effects with those obtained with the use of thapsigargin, an inhibitor of sarcoplasmic/ER $Ca^{2+}$-ATPases that is frequently used as a strong model inducer of the ESR. Cells were treated with either DMC or thapsigargin for various times in parallel, and the expression levels of CHOP, GRP78, and caspase-4, an ESR-specific caspase, were analyzed. FIG. 4 shows that DMC and thapsigargin stimulated the three selected ESR indicators in a similar fashion. Both CHOP and GRP78 were substantially elevated, with a prominent increase noted at the 6-h time point and thereafter. Activation of caspase-4, which was indicated by the appearance of the cleaved (activated) form of this enzyme, was first noted at ~24 h of drug treatment and persisted until the later (36 h) time point. Thus, the stimulation of the ESR was remarkably similar between DMC and the model inducer thapsigargin, suggesting that the effects of DMC were quite potent in this context.

A prominent feature of the ESR is a general, transient down-regulation of overall protein synthesis, in combination with selectively increased translation of ER stress proteins, such as GRP78 (33, 34). We therefore investigated whether DMC and celecoxib would impair cellular translation by determining the incorporation of 35S-methionine into newly translated proteins. As shown in FIG. 5, both drugs severely diminished the rate of translation in a concentration-dependent manner, with DMC being noticeably more potent. At 2 h of treatment, 60 µmol/L DMC and 80 µmol/L celecoxib were as effective as thapsigargin, and nearly as effective as the potent translational inhibitor cycloheximide, and reduced ongoing translation by ~90%. This inhibitory effect was transient, as cells returned to unrestricted, fully active protein synthesis by 18 h, despite the continuous presence of DMC or celecoxib (FIG. 5; data not shown for celecoxib). In addition, greatly increased translation of GRP78 could be detected in DMC- and celecoxib-treated cells (FIG. 5; data not shown for celecoxib). Taken together, these results show that DMC and celecoxib cause the typical features of ESR in drug-treated cells.

Due to the striking similarities between the effects of DMC/celecoxib and those of thapsigargin, which is known to leak calcium from the ER and generate a calcium spike in the cytoplasm, we next determined whether DMC, and several coxibs and NSAIDs in comparison, would induce such a response as well. For this purpose, cells were loaded with Fura-2/AM, exposed to 100 µmol/L of each drug, and the increase in cytoplasmic calcium levels was measured. As shown in FIG. 6, DMC and celecoxib caused a pronounced calcium spike, which could be observed in each and every cell tested. In contrast, none of the other coxibs (rofecoxib and valdecoxib) or traditional NSAIDs (flurbiprofen, indomethacin, and sulindac) were able to elicit an elevation of cytoplasmic calcium levels. Thus, DMC and celecoxib seemed to be uniquely able to mimic this aspect of thapsigargin, and the potent elevation of intracytoplasmic calcium levels by these drugs is entirely consistent with the generation of ESR, as documented in FIGS. 3-5 above. The average maximum calcium peak (FIG. 6B) caused by DMC was somewhat greater than what was measured for celecoxib, but this difference was not statistically significant; however, overall calcium release (FIG. 6A; area under the curve) was consistently 30% to 50% larger with DMC.

To further substantiate the uniqueness of DMC and celecoxib compared with other coxibs and NSAIDs, we next investigated how the observed effects of these two drugs would compare with those of other coxibs and traditional NSAIDs. First, we treated cells with DMC and the three coxibs celecoxib, rofecoxib, and valdecoxib and determined the expression levels of the ER stress indicator protein CHOP. At 50 µmol/L, DMC generated a pronounced induction of CHOP, which was detectable as early as 4 h after the onset of drug treatment and continued to increase up to 24 h (FIG. 6A). Treatment of cells with 50 µmol/L celecoxib resulted in a similar kinetic of CHOP induction, although the overall levels were noticeable lower compared with DMC. In contrast, neither rofecoxib nor valdecoxib at the same concentration resulted in any detectable CHOP expression (FIG. 7A).

To investigate whether ESR induction could possibly be achieved at higher concentrations of rofecoxib and valdecoxib, the cells were treated with further increased concentrations of each drug. However, as shown in FIG. 7B, even at concentrations of 75 or 100 µmol/L, neither rofecoxib nor valdecoxib was able to stimulate any detectable increase in either CHOP or GRP78 protein. In comparison, DMC and celecoxib potently induced the expression of both of these proteins, and once again, DMC.

We next investigated the relationship of ER stress induction and cell death. FIG. 8A shows that 30 and 50 µmol/L DMC potently stimulated the ESR, as indicated by the pronounced induction of CHOP, GRP78, and caspase-4 cleavage/activation. In parallel, three variables of cell growth and cell death were investigated. First, a colony-forming assay was done; this is an indicator of longterm survival that reveals the percentage of individual cells that are able to survive and spawn a colony of new cell growth. Second, the traditional 3-(4,5-dimethylthiazol-2-yl)-2,5-diphenyltetrazolium bromide assay was used to determine short-term growth and survival, indicated primarily by the metabolic activity of the entire cell population. Third, terminal deoxynucleotidyl transferase-mediated dUTP nick end labeling assay was done to quantify the fraction of cells undergoing apoptosis. As shown in FIG. 6A, the induction of ESR by DMC closely correlated with greatly reduced survival in colony-forming assays, with reduced cellular activity in 3-(4,5-dimethylthiazol-2-yl)-2,5-diphenyltetrazolium bromide assays, and with substantially increased apoptosis.

Celecoxib as well was able to induce cell death/apoptosis (FIG. 8B) and reduced the viability of the cell culture (FIG. 8C), although its potency was clearly less than that of DMC (as indicated by the requirement of higher concentrations). However, none of the other coxibs (rofecoxib and valdecoxib) or traditional NSAIDs (flurbiprofen, indomethacin, and sulindac) had any detectable effect on cell growth and survival and did not induce apoptosis even at concentrations of up to 100 µmol/L (FIGS. 8B and C). Thus, taken together, these results indicate that celecoxib is unique among these coxibs/NSAIDs because of its superior potency to stimulate the ESR and initiate tumor cell death; in addition, its derivative DMC seems even more effective, clearly arguing that the inhibition of COX-2 is not required to achieve these effects.

We next investigated the contribution of the ESR to reduced tumor cell growth in response to treatment with DMC or celecoxib. For this purpose, we applied specific siRNAs to knock down the expression of either GRP78 (representing the protective branch of the ESR) or caspase-4 (representing the proapoptotic branch). Glioblastoma cells were transfected with these siRNAs and treated with drug for 48 h, and the percentage of surviving cells was determined with the use of the colony formation assay (FIG. 9A). As a control, a si-GFP was included in these experiments; furthermore, the efficiency of target knockdown by each specific siRNA was confirmed by Western blot analysis of caspase-4 and GRP78 protein (FIG. 9B). For GRP78-siRNA, the cells became more sensitive and there was less cell survival when GRP78 levels were reduced. For caspase-siRNA, the opposite was observed: we found that the sensitivity of cells to drug treatment was significantly reduced (i.e., cell survival after treatment with celecoxib or DMC was increased when caspase-4 expression was diminished by siRNA). Thus, these results agree with the current model of ESR, where GRP78 represents the protective arm, whereas caspase-4 is proapoptotic and necessary for the execution of cell death after ER stress; our results indicate that DMC and celecoxib overpower the protective effort by GRP78 and induce cell death via the stimulation of caspase-4 activity.

In an effort to determine whether ER stress might be relevant during the in vivo antitumor activity of DMC, we used a xenograft nude mouse tumor model and investigated the expression of CHOP protein in tumor tissue from animals treated with DMC or rofecoxib. As shown in FIG. 10, CHOP protein was barely detectable in tumor tissue from control animals (i.e., in the absence of any drug treatment). In contrast, when animals were fed with DMC for 50 h, there was a large increase in CHOP protein expression in their tumor tissue. In comparison, when animals received rofecoxib, no such increase was observed (FIG. 10). In addition, the highly elevated amount of CHOP protein after DMC treatment correlated with significantly increased apoptosis in the tumor tissue, whereas tumors from rofecoxib-treated animals did not display elevated levels of apoptosis (FIG. 10). Furthermore, on longer-term therapy of tumor-bearing animals with either DMC or rofecoxib, it became apparent that only DMC caused significantly reduced tumor growth (FIG. 11), indicating that the induction of ESR and apoptosis by DMC indeed translated into overall reduced tumor growth in this xenograft model.

Finally, as an extension of earlier pharmacokinetic/pharmacodynamic determinations of DMC and celecoxib in nude mice (20), we measured the concentration of drug (DMC and celecoxib) in blood and tumor tissues from our experimental animals. Tumor-bearing animals were treated for 2 days with daily dosages ranging from 30 to 180 mg/kg DMC or celecoxib, and the absolute levels ($C_{max}$) of each drug were determined by liquid chromatography mass spectrometry. As presented in the Table 2, maximal drug concentrations in plasma and tumor tissue increased as daily dosages increased and reached peak levels of 45 μmol/L in the plasma from animals treated with the highest dose of 180 mg/kg. Intriguingly, however, the concentrations in tumor tissues were two orders of magnitude lower than the corresponding plasma concentrations; in animals receiving the highest daily dose of 180 mg/kg, tumor tissue concentrations approximately equivalent to only 0.25 μmol/L were reached. Nonetheless, in all of these tumor tissues, increased levels of CHOP expression were observed, whereas tumor tissues from non-drug treated or rofecoxib treated (30-180 mg/kg) animals were consistently negative for this ER stress indicator protein (see FIG. 10). In general, tumor tissues from animals treated with the lowest dosages of DMC or celecoxib were positive for CHOP, although tumors from those animals exposed to much higher concentrations stained more intensely for this protein. Importantly, these results show that despite the huge difference between the drug concentrations used in vitro and those measured in vivo, in both cases, ER stress and subsequent tumor cell death were achieved.

Example 2

Aggravated Endoplasmic Reticulum Stress as a Basis for Enhanced Glioblastoma Cell Killing by Bortezomib in Combination with Celecoxib or its Non-Coxib Analogue, 2,5-Dimethyl-Celecoxib Materials and Methods
Materials Bortezomib was obtained from the pharmacy as 3.5 mg Velcade suspended in 3.5 mL saline (Millennium Pharmaceuticals). Celecoxib was obtained as capsules from the pharmacy or synthesized in our laboratory according to previously published procedures (24). DMC is a close structural analogue of celecoxib, where the 5-aryl moiety has been altered by replacing 4-methylphenyl with 2,5-dimethylphenyl; this compound was synthesized in our laboratory according to previously published procedures (19). Celecoxib and DMC were dissolved in DMSO at 100 mmol/L (stock solution) and added to the cell culture medium in a manner that kept the final concentration of solvent below 0.1%. The COX-2-inhibitory activity of freshly synthesized celecoxib, and lack thereof in DMC, was confirmed in vitro with the use of purified COX-2 protein (see, for example, ref. 42).

Cell Lines and Culture Conditions

All cells were propagated in DMEM (Cellgro) supplemented with 10% fetal bovine serum, 100 units/mL penicillin, and 0.1 mg/mL streptomycin in a humidified incubator at 37° C. and a 5% $CO_2$ atmosphere. Four human glioblastoma cell lines (LN229, U251, T98G, and U87MG) and one multiple myeloma cell line (RPMI/8226) were used. T98G, U87MG, and RPMI/8226 cells were obtained from the American Type Culture Collection. LN229 and U251 were obtained from Frank B. Furnari (Ludwig Institute of Cancer Research, La Jolla, Calif.). COX-2 expression levels and drug effects on prostaglandin production in these cells have been published elsewhere.

3-(4,5-Dimethylthiazol-2-yl)-2,5-diphenyltetrazolium bromide assay 3-(4,5-Dimethylthiazol-2-yl)-2,5-diphenyltetrazolium bromide (MTT) assays were performed in 96-well plates with the use of $3.0 \times 10^3$ to $8.0 \times 10^3$ cells per well as described in detail elsewhere (19).

Cell Death ELISA

Cells were plated in 96-well plates in quadruplicates at 1,000 cells/mL (100 μL/well). The next day, they were treated with drugs for 24 h and analyzed for the presence of histone-complexed DNA fragments with the use of a commercially available ELISA kit (Roche Diagnostics) according to the manufacturer's instructions. The kit was used in a manner as to specifically quantitate apoptosis rather than necrosis.

Immunoblots and Immunohistochemical Staining

Total cell lysates were prepared and analyzed by Western blot analysis as described earlier (19). Immunohistochemical analysis of protein expression in tumor tissues was performed with the use of the Vectastain avidin-biotin complex method kit (Vector Laboratories) as described previously (32). The primary antibodies were purchased from Cell Signaling Technology or Santa Cruz Biotechnology, Inc. and used according to the manufacturers' recommendations. All immunoblots and stainings were repeated at least once to confirm the results.

Terminal Deoxynucleotidyl Transferase-Mediated dUTP Nick End Labeling Staining of Tumor Tissue Apoptosis in tumor sections was measured quantitatively with the use of the terminal deoxynucleotidyl transferase-mediated dUTP nick end labeling (TUNEL) assay. All components for this procedure were from the ApopTag In Situ Apoptosis Detection kit (Chemicon), which was used according to the manufacturer's instructions. The percentage of TUNEL-positive cells for each tumor section was determined from 10 random photomicrographs taken at 200 magnification.

Transfections and Colony Formation Assay

The different small interfering RNAs (siRNA) were synthesized at the microchemical core laboratory of the University of Southern California/Norris Comprehensive Cancer Center; their sequences are described in ref. 32. Transfections of cells with these siRNAs and subsequent analysis of cell survival by colony formation assay have been described in detail elsewhere (32).

Drug Treatment of Nude Mice

Four- to 6-week-old male athymic nu/nu mice were obtained from Harlan and implanted s.c. with $5 \times 10^5$ U87 glioblastoma cells. Once tumors of ~300 mm$^3$ had developed, the animals received drug treatments. Velcade was given as a single dose via tail vein injection. DMC was given twice daily (one half of the daily dose every 12 h) via direct administration into the stomach with a stainless steel ball-head feeding needle (Popper and Sons, Inc.). After a total of 50 h, the animals were sacrificed and tumors were collected for analysis. In all experiments, the animals were closely monitored with regards to body weight, food consumption, and clinical signs of toxicity; no differences between non-drug-treated control animals and drug-treated animals were detected.

Results

Glioblastoma multiforme represents a particularly difficult-to-treat type of cancer with dismal prognosis. Because more effective therapies are urgently needed, we chose various human glioblastoma cell lines as a model to investigate combination effects of our selected drugs. To establish the concentration of each drug that would result in 50% inhibition of cell growth ($IC_{50}$), we first treated each cell line individually with either bortezomib, celecoxib, or the non-coxib celecoxib analogue DMC. The resulting $IC_{50}$ after 48 h of treatment with bortezomib was ~10 nmol/L for the U251, U87MG, and T98G glioblastoma cell lines and slightly below 5 nmol/L for the LN229 glioblastoma cell line (FIG. 12A). Because bortezomib was developed for multiple myeloma therapy and is highly cytotoxic in such tumor cell lines, we also determined its $IC_{50}$ in a representative multiple myeloma cell line, RPMI/8226, for comparison purposes. As shown in FIG. 12A, and as expected, RPMI/8226 cells exhibited high sensitivity toward bortezomib; however, this cell type was not more sensitive than the glioblastoma cell lines. This finding established that glioblastoma cells were exquisitely sensitive to bortezomib, which supported our rationale for investigating this drug as a potential glioblastoma therapy.

We also established the $IC_{50}$ for celecoxib and DMC in all four glioblastoma cell lines (FIGS. 12A and B). Celecoxib displayed an $IC_{50}$ of ~50 µmol/L in U251, U87MG, and T98G cells, whereas DMC was somewhat more potent with an $IC_{50}$ of slightly below 40 µmol/L. The LN229 cell line (which exhibited the greatest sensitivity to bortezomib; FIG. 12A) was overall slightly less sensitive to either celecoxib or DMC (FIGS. 12A and B).

To determine the ability of bortezomib, celecoxib, and DMC to induce the ESR in glioblastoma cells, we treated U251 cells with increasing concentrations of each drug increased expression of GRP78 and CHOP, indicating that the ESR was triggered. In addition, this drug also stimulated the activation of the ER stress-associated procaspase-4, as indicated by the appearance of the cleaved (i.e., activated) form of this enzyme. To verify that bortezomib, at the concentrations we used, exerted its established function (i.e., inhibition of the proteasome), we also investigated the accumulation of polyubiquitinated proteins. As shown in FIG. 13A, the induction of ER stress markers coincided with the appearance of highly elevated levels of polyubiquitinated proteins, indicating that inhibition of the proteasome correlated with the induction of ER stress.

The same targets were also investigated after treatment of cells with either celecoxib or DMC. In all our experiments, celecoxib and DMC consistently generated the same outcome, except that DMC was slightly more potent [for this reason, and also because the induction of ER stress by celecoxib has been reported earlier, we will focus primarily on the results obtained with DMC]. As shown in FIG. 3B, DMC treatment resulted in strong induction of GRP78 and CHOP and activation of caspase-4, indicating that this drug triggered ER stress. However, this drug did not cause substantial accumulation of polyubiquitnated proteins, consistent with the expectation that its mechanism of action was different from that of bortezomib.

We next examined the effects of combination drug treatments on glioblastoma cell growth and survival. For this purpose, we combined bortezomib with either celecoxib or DMC at concentrations that represented approximate $IC_{50}$ values so that potentially enhancing effects would become apparent. FIG. 14A depicts a visual display of cell number and morphology, whereas FIG. 14B presents the quantified outcome. FIG. 14A reveals that individual drug treatment resulted in a smaller increase in cell number and the presence of fewer mitotic figures; in contrast, combination drug treatment resulted in noticeable cell loss and apparent cell death. These visual impressions were complemented by counting the number of viable cells over the course of drug treatment (at 8, 24, and 48 h). As displayed in FIG. 14B, single-drug treatment allowed initial cell proliferation (i.e., increase in cell numbers between 8 and 24 h) and then exerted presumed cytostatic effects (i.e., the overall number of cells did not change between 24 and 48 h). In contrast, when the drugs were applied in combination, there was no increase in cell numbers at the 24-h time point and substantial loss of viable cells between 24 and 48 h, indicating potent cytotoxic effects.

The extent of drug-induced cell death and survival was further investigated by cell death ELISA, which quantitates the amount of apoptosis in the entire culture, and by colony formation assays, which determine the number of individual cells able to survive drug treatment long-term and spawn a colony of clonal descendants. FIG. 14C shows that treatment of glioblastoma cells with individual drugs caused a small increase in apoptotic cell death, whereas the combined treatment with bortezomib and celecoxib or DMC resulted in greatly increased cell death. In colony formation assays, 5 nmol/L bortezomib reduced the number of emerging colonies by ~50% (FIG. 14D). The chosen concentrations of celecoxib and DMC by themselves exerted only minor inhibitory effects (reduction of colony number by approximately 10-15%). In contrast, when cells were treated with bortezomib and celecoxib or DMC in combination, colony survival was greatly reduced by >90% and 97%, respectively.

Each assay used in FIG. 14 was applied to several different glioblastoma cell lines and varying concentrations of drug combinations were used (data not shown). In all cases, very similar outcomes were achieved, clearly indicating that the combination of these drugs results in greatly increased cytotoxicity and substantially reduced cell survival compared with treatment with each drug individually. Furthermore, we calculated the combination index (CI) from conventional MTT assays where increasing concentrations of each drug were combined (data not shown) and obtained a CI<1, revealing that the drug combination effects were synergistic.

We next investigated the potential contribution of the ESR to the above-presented combination drug effects. U87MG and T98G cells were treated with the same drug combinations as above, and various components of the ESR system and cell death machinery were analyzed. As shown in FIG. 15, individual drug treatments resulted in increased expression of GRP78, and combination drug treatments increased expression of this protein further. Levels of the proapoptotic CHOP protein were weakly increased by single-drug treatments but were more strongly elevated by combination treatments. The activity of c-Jun NH2-terminal kinase (JNK), a critical proapoptotic component of the ESR, was investigated with antibodies specifically recognizing the phosphorylated (i.e., active) form of this kinase. We found that combination drug treatments, but not individual drug treatments, resulted in greatly increased JNK activity (FIG. 15A). Taken together, these results indicate that bortezomib, when combined with either celecoxib or DMC, caused stronger ESR induction than either drug alone. Similar results were also obtained with the use of LN229 and U251 cells (data not shown).

To establish whether drug-induced ER stress and cellular apoptosis were only correlative or were causally related, we specifically reduced the expression of the ESR component GRP78. If drug-induced cell death was controlled by the ESR, we would expect that reduced levels of GRP78, which functions as a major protective component of the ESR, would lead to further increased cell death. U251 cells were transfected with siRNA against GRP78; as a control, cells were transfected with siRNA against a target not present in mammalian cells [i.e., green fluorescent protein (GFP)]. Both siGRP78-transfected and siGFP-transfected cells were treated with bortezomib together with celecoxib or DMC, and the number of surviving cells was determined by colony formation assay. As shown in FIG. 16A, cell survival was significantly ($P<0.002$) decreased in cells harboring reduced levels of GRP78; cell survival after drug treatment was 63% to 68% in cells transfected with siGFP but was decreased to 40% to 42% in cells transfected with siGRP78. Down-regulation of GRP78 expression by siGRP78 was confirmed by Western blot analysis; however, whereas the presence of siGRP78 reduced basal levels of GRP78 below the detection limit, the siRNA could not completely block the induction of GRP78 by drug treatment, as lower levels of induced GRP78 protein could still be detected (FIG. 16B). Nonetheless, under all conditions, the overall amount of GRP78 protein was lower in siGRP78-transfected cells than in siGFP-transfected cells. Concurrently, siGRP78-transfected cells exhibited significantly increased chemosensitivity, indicating that the ESR played a causal role in triggering cell death induced by bortezomib in combination with celecoxib or DMC.

Finally, we determined whether the above-described in vitro events would also take place in vivo. U87MG cells were implanted s.c. into nude mice, and after sizable tumors had formed, the animals remained untreated or were treated with drugs. Celecoxib was not included in this experiment because previous studies had already shown that this drug potently stimulated the ESR in vivo (39, 40); furthermore, all known experiments that compared DMC to celecoxib have shown that both drugs reliably achieve the same tumor-suppressive outcome in vitro and in vivo, except that DMC consistently displays somewhat greater apoptosis-inducing potency. Therefore, we decided on DMC as the more potent drug of choice for the in vivo combination experiments with bortezomib.

We had shown previously that DMC by itself quite potently triggers ER stress in tumor tissue in vivo (39), and this effect begins to appear at dosages of >10 mg/kg. Considering these earlier results, we chose 7.5 mg/kg as a potentially useful dosage for this combination experiment; we reasoned that suboptimal dosages of DMC would allow the combination effects to emerge. Tumor bearing animals were treated with DMC or bortezomib alone or in combination for 2 days (a relatively short treatment period was chosen because we wanted to focus on the early mechanisms that initiate cell death rather than the later conditions that dominate when the tumor cells are dying or already are dead). Tumor tissue was analyzed for the expression of CHOP (as a marker of ER stress) and stained by TUNEL (to visualize the extent of apoptotic cell death).

We found that DMC, at this very low dosage, did not cause much elevated CHOP expression nor did it substantially increase TUNEL staining (FIG. 17A). Bortezomib treatment by itself resulted in a larger fraction of CHOP-positive cells, concomitant with increased TUNEL staining. In comparison, when bortezomib was given together with DMC, there was a very strong induction of CHOP, which could be detected in every single cell, and an even greater increase in the number of TUNEL-positive cells (FIG. 17A). When the number of TUNEL-positive cells in the various treatment groups was quantitated, it became apparent that combination treatment resulted in significantly more cell death than individual drug treatment (FIG. 17B); that is, cell death in response to treatment with bortezomib plus DMC was 4.9- and 3.0-fold higher than in animals treated with DMC or bortezomib alone, respectively. Thus, combination drug treatment resulted in substantially higher levels of ER stress and a greater amount of cell death than individual drug treatments and established that aggravated ER stress and enhanced glioblastoma cell killing could be achieved in vivo as well.

Example 3

Aggravated Endoplasmic Reticulum Stress as a Basis for Enhanced Cell Killing of Tumor-Associated Brain Endothelial Cells by Temozolomide in Combination with the Non-Coxib Celecoxib Analogue, 2,5-Dimethyl-Celecoxib (DMC)

Materials and Methods

Tumor-associated Brain Endothelial Cells (TuBEC) were treated with TMZ (300 uM) and 20 uM DMC for 48 hours. The drugs were removed and cells were incubated for another 12 days; at that time cytotoxicity was evaluated using the trypan blue exclusion technique. Results are presented as number of viable cells per group.

Results

Temozolomide (TMZ), the standard of treatment for gliomas, is very effective against the tumor cells. However, this drug causes little cytotoxicity on the tumor-associated brain endothelial cells (TuBEC). Our experiments, summarized in FIG. 18 have shown that the ER aggravating agent DMC increased the susceptibility of the tumor vascular endothelial cells susceptible to TMZ. Thus DMC functions as an anti-angiogenic agent by chemosensitizing these cells to known therapeutic drugs.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the appended claims.

TABLE 1

Apoptosis-triggering Strategies

| Strategy | Target | Approach | Stage of development |
|---|---|---|---|
| Proapoptotic approaches | | | |
| Introduction of proapoptotic players | TRAIL | Recombinant protein | Clinical trials planned |
| | Apoptin | Gene therapy | Preclinical |
| | Caspases | Gene therapy | Preclinical |
| Modulation of antiapoptotic genes or pathways | Mitochondria: Proapoptotic molecules (Bax, BCL-Xs) | Gene therapy | Preclinical |
| | Downregulate antiapoptotic molecules (Bcl-2, Bcl-XL) | ODNs | Phase II/III |
| | Direct effect on mitochondria | Lonidamine, arsenite | Phase III |
| | Direct effect on pores | PK 11195 | Preclinical |
| Restoration or manipulation of tumor suppressor genes | p53 | Gene therapy | Phase II/III |
| | Retinoblastoma | Gene therapy | Preclinical |
| | FHIT | Gene therapy | Clinical trials planned |
| Permissive approaches | | | |
| Oncogenes | PI3k | LY294002 | Preclinical |
| | Ras | Small molecules, ODNs | Phase II/III |
| | BCR-ABL | Small molecule (STI-571) | Phase III |
| | NFκB | ODNs | Phase I/II |
| | Proteasome inhibitors | PS-341 | Phase II |
| | c-raf | ODNs | Phase II |
| | c-myb | ODNs | Preclinical |
| | Cell cycle modulators | UCN-01, flavopiridol | Phase III |

TABLE 2

Drug concentrations in plasma and tumor tissue

| Animal no. | Drug and dosage, mg/kg/d | Maximum plasma levels*, µg/L (µmol/L) | Tumor tissue levels*, ng/mg (approximately µmol/L) |
|---|---|---|---|
| 1 | No drug treatment | <0.5† | <0.2‡ |
| 2 | Cxb 30 | 6,950 (18.2) | 17.53 (0.046) |
| 3 | Cxb 90 | 9,450 (24.8) | 44.03 (0.116) |
| 4 | Cxb 150 | 14,000 (36.8) | 61.23 (0.161) |
| 5 | Cxb 180 | 17,000 (44.6) | 94.78 (0.249) |
| 6 | DMC 30 | 3,035 (7.6) | 8.27 (0.021) |
| 7 | DMC 90 | 3,190 (8.0) | 14.44 (0.037) |
| 8 | DMC 150 | 9,500 (23.8) | 39.04 (0.099) |
| 9 | DMC 180 | 18,200 (45.5) | 110.42 (0.280) |

Abbreviation: Cxb, celecoxib.
*Average of two measurements.
†Detection limit in blood was ~5 µg/L
‡Detection limit in tumor tissue was ~5 ng/mg.

REFERENCES

1. Kerr, J. F., Wyllie, A. H., and Currie, A. R. Apoptosis: a basic biological phenomenon with wide-ranging implications in tissue kinetics. Br. J. Cancer, 26: 239-257, 1972.
2. Hengartner M. O. The biochemistry of apoptosis. Nature, 407: 770-776, 2000.
3. Thompson C. B. Apoptosis in the pathogenesis and treatment of disease. Science, 267: 1456-1462, 1995.
4. Ferreira G. C., et al., Clinical Cancer Research Vol. 8, 2024-2034, July 2002.
5. Boyce M, Yuan J. Cellular response to endoplasmic reticulum stress: a matter of life or death. Cell Death Differ 2006; 13:363-73.
6. Wu J, Kaufman R J. From acute ER stress to physiological roles of the unfolded protein Response. Cell Death Differ 2006; 13:374-84.
7. Ulrich C M, Bigler J, Potter J D. Non-steroidal anti-inflammatory drugs for cancer prevention: promise, perils, and pharmacogenetics. Nat Rev Cancer 2006; 6:130-40.
8. Hitomi J, Katayama T, Eguchi Y, et al. Involvement of caspase-4 in endoplasmic reticulum stress-induced apoptosis and Ah-induced cell death. J Cell Biol 2004; 165: 347-56.
9. Oyadomari S, Mori M. Roles of CHOP/GADD153 in endoplasmic reticulum stress. Cell Death Differ 2004; 11:381-9.
10. Parente L, Perretti M. Advances in the pathophysiology of constitutive and inducible cyclooxygenases: two enzymes in the spotlight. Biochem Pharmacol 2003; 65:153-9.
11. Yoshida H, Okada T, Haze K, Yanagi H, Yura T, Negishi M and Mori K (2001) Endoplasmic reticulum stress-induced formation of transcription factor complex ERSF including NF-Y (CBF) and activating transcription factors 6alpha and 6beta that activates the mammalian unfolded protein response. Mol. Cell. Biol. 21: 1239-1248.
12. Yoshida H, Matsui T, Yamamoto A, Okada T and Mori K (2001) XBP1 mRNA is induced by ATF6 and spliced by IRE1 in response to ER stress to produce a highly active transcription factor. Cell 107: 881-891.
13. Calfon M, Zeng H, Urano F, Till J H, Hubbard S R, Harding H P, Clark S G and Ron D (2002) IRE1 couples endoplasmic reticulum load to secretory capacity by processing the XBP-1 mRNA. Nature 415: 92-96
14. Lee K, Tirasophon W, Shen X, Michalak M, Prywes R, Okada T, Yoshida H, Mori K and Kaufman R J (2002) IRE1-mediated unconventional mRNA splicing and S2P-mediated ATF6 cleavage merge to regulate XBP1 in signaling the unfolded protein response. Genes Dev. 16: 452-466
15. Wang Y, Shen J, Arenzana N, Tirasophon W, Kaufman R J and Prywes R (2000) Activation of ATF6 and an ATF6 DNA binding site by the endoplasmic reticulum stress response. J. Biol. Chem. 275: 27013-27020
16. Ubeda M and Habener J F (2000) CHOP gene expression in response to endoplasmic-reticular stress requires NFY interaction with different domains of a conserved DNA-binding element. Nucleic Acids Res. 28: 4987-4997
17. Arico S, Pattingre S, Bauvy C, et al. Celecoxib induces apoptosis by inhibiting 3-phosphoinositide-dependent protein kinase-1 activity in the human colon cancer HT-29 cell line. J Biol Chem 2002; 277: 27613-21.
18. Hanif R, Pittas A, Feng Y, et al. Effects of nonsteroidal anti-inflammatory drugs on proliferation and on induction of apoptosis in colon cancer cells by a prostaglandin-independent pathway. Biochem Pharmacol 1996; 52:237-45.
19. Kardosh A, Blumenthal M, Wang W J, et al. Differential effects of selective COX-2 inhibitors on cell cycle regulation and proliferation of glioblastoma cell lines. Cancer Biol Ther 2004; 3:9-16.
20. Kulp S K, Yang Y T, Hung C C, et al. 3-Phosphoinositide-dependent protein kinase-1/Akt signaling represents a major cyclooxygenase-2-independent target for celecoxib in prostate cancer cells. Cancer Res 2004; 64:1444-51.
21. Shureiqi I, Chen D, Lotan R, et al. 15-Lipoxygenase-1 mediates nonsteroidal anti-inflammatory drug-induced apoptosis independently of cyclooxygenase-2 in colon cancer cells. Cancer Res 2000; 60:6846-50.
22. Tegeder I, Pfeilschifter J, Geisslinger G. Cyclooxygenase-independent actions of cyclooxygenase inhibitors. FASEB J 2001; 15:2057-72.
23. Zhang X, Morham S G, Langenbach R, et al. Malignant transformation and antineoplastic actions of nonsteroidal antiinflammatory drugs (NSAIDs) on cyclooxygenase-null embryo fibroblasts. J Exp Med 1999; 190:451-9.
24. Penning T D, Talley J J, Bertenshaw S R, et al. Synthesis and biological evaluation of the 1,5-diarylpyrazole class of cyclooxygenase-2 inhibitors: identification of 4-[5-(4-methylphenyl)-3-(trifluoromethyl)-1H-pyrazol-1-yl]benzenesulfonamide (SC-58635, celecoxib). J Med Chem 1997; 40: 1347-65.
25. Talley J J, Brown D L, Carter J S, et al. 4-[5-Methyl-3-phenylisoxazol-4-yl]-benzenesulfonamide, valdecoxib: a potent and selective inhibitor of COX-2. J Med Chem 2000; 43:775-7.
26. Chan C C, Boyce S, Brideau C, et al. Rofecoxib [Vioxx, MK-0966; 4-(4'-methylsulfonylphenyl)-3-phenyl-2-(5H)-furanone]: a potent and orally active cyclooxygenase-2 inhibitor. Pharmacological and biochemical profiles. J Pharmacol Exp Ther 1999; 290:551-60.
27. Prasit P, Wang Z, Brideau C, et al. The discovery of rofecoxib, [MK 966, Vioxx, 4-(4'-methylsulfonylphenyl)-3-phenyl-2(5H)-furanone], an orally active cyclooxygenase-2-inhibitor. Bioorg Med Chem Lett 1999; 9: 1773-8.
28. Harlow E, Lane D. Using antibodies: a laboratory manual. Cold Spring Harbor, N.Y.: Cold Spring Harbor Laboratory Press, 1999. p. 267-309.
29. Wu R-C, Schönthal A H. Activation of p53-21waf1 pathway in response to disruption of cell-matrix interactions. J Biol Chem 1997; 272:29091-8.
30. Heatwole V M. TUNEL assay for apoptotic cells. Methods Mol Biol 1999; 115:141-8.
31. Grynkiewicz G, Poenie M, Tsien R Y. A new generation of $Ca^{2+}$ indicators with greatly improved fluorescence properties. J Biol Chem 1985; 260:3440-50.
32. Pyrko P, Soriano N, Kardosh A, et al. Downregulation of surviving, expression and concomitant induction of apoptosis by celecoxib and its non-cyclooxygenase-2-inhibitory analog, dimethyl-celecoxib (DMC), in tumor cells in vitro and in vivo. Mol Cancer 2006; 5:19.
33. Luo S, Baumeister P, Yang S, et al. Induction of Grp78/BiP by translational block: activation of the Grp78 promoter by ATF4 through and upstream ATF/CRE site independent of the endoplasmic reticulum stress elements. J Biol Chem 2003; 278:37375-85.
34. Ma Y, Hendershot L M. The role of the unfolded protein response in tumour development: friend or foe? Nat Rev Cancer 2004; 4:966-77.
35. Kim S H, Hwang C I, Park W Y, et al. GADD153 mediates celecoxib induced apoptosis in cervical cancer cells. Carcinogenesis 2006; 28: 223-31.
36. Trifan O C, Durham W F, Salazar V S, et al. Cyclooxygenase-2 inhibition with celecoxib enhances antitumor efficacy and reduces diarrhea side effect of CPT-11. Cancer Res 2002; 62:5778-84.
37. Roh J L, Sung M W, Park S W, et al. Celecoxib can prevent tumor growth and distant metastasis in postoperative setting. Cancer Res 2004; 64:3230-5.
38. Williams C S, Watson A J, Sheng H, et al. Celecoxib prevents tumor growth in vivo without toxicity to normal gut: lack of correlation between in vitro and in vivo models. Cancer Res 2000; 60:6045-51.
39. Tegeder I, Pfeilschifter J, Geisslinger G. Cyclooxygenase-independent actions of cyclooxygenase inhibitors. FASEB J 2001; 15:2057-72.
40. Backhus L M, Petasis N A, Uddin J, et al. Dimethyl-celecoxib as a novel non-COX-2 therapy in the treatment of lung cancer. J Thorac Cardiovasc Surg 2005; 130:1406-12.
41. Johnson A J, Song X, Hsu A, et al. Apoptosis signaling pathways mediated by cyclooxygenase-2 inhibitors in prostate cancer cells. Adv Enzyme Regul 2001; 41:221-35.
42. Schonthal A H. Antitumor properties of dimethyl celecoxib, a derivative of celecoxib that does not inhibit cyclooxygenase-2: implications for glioblastoma therapy. NeurosurgicalFocus 2006; 20:1-10.

What is claimed is:

1. A method of treating a cancer or a cancer-related condition in a patient by triggering apoptosis in selected cancer cells, comprising administering a pharmaceutically effective amount of a compound that can induce or aggravate ER stress in the diseased cells by mildly inhibiting SERCA, wherein:

the compound has a general formula:

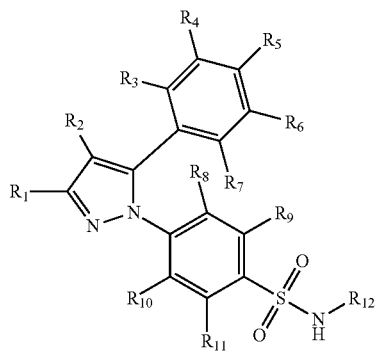

wherein,
- $R_1$ is methyl, fluoromethyl, difluoromethyl, trifluoromethyl, alkyl, fluoroalkyl, difluoroalkyl, trifluoroalkyl, polyfluoroalkyl, hydroxyalkyl, or carboxyalkyl;
- $R_2$ is hydrogen, fluoro, chloro, bromo; fluoromethyl, difluoromethyl, trifluoromethyl, alkyl, fluoroalkyl, difluoroalkyl, trifluoroalkyl, polyfluoroalkyl, hydroxyalkyl, or carboxyalkyl;
- $R_3$-$R_7$ are independently selected from a group consisting of: hydrogen, fluoro, chloro, bromo, alloxy, alkyl, fluoroalkyl, difluoroalkyl, trifluoroalkyl, polyfluoroalkyl, hydroxyalkyl, or carboxyalkyl, aryl and heteroaryl;
- $R_8$-$R_{11}$ are independently selected from a group consisting of: hydrogen, fluoro, chloro, bromo; fluoromethyl, difluoromethyl, trifluoromethyl, alkyl, fluoroalkyl, difluoroalkyl, trifluoroalkyl, polyfluoroalkyl, hydroxyalkyl, carboxyalkyl, alkenyl, alkynyl, cycloalkyl, heterocyclic, aryl, or heteroaryl; and
- $R_{12}$ is hydrogen, acetyl, acyl, alkyl, fluoroalkyl, difluoroalkyl, trifluoroalkyl, polyfluoroalkyl, hydroxyalkyl, carboxyalkyl; aminoacyl, aminoalkyl, cycloalkyl, heterocyclic, aryl, or heteroaryl, with the proviso that the compound 4-[5-(4-methylphenyl)-3-(trifluoromethyl)pyrazol-1-yl]benzenesulfonamide is excluded.

2. The method of claim 1, wherein $R_1$ is trifluoromethyl.

3. The method of claim 1, wherein $R_1$ is trifluoromethyl, $R_2$, $R_4$, $R_5$, $R_7$ $R_8$, $R_9$, $R_{10}$, and $R_{11}$ are hydrogen.

4. The method of claim 1, wherein $R_3$ and $R_6$ are selected from a group consisting of: fluoro, chloro, bromo; fluoromethyl, difluoromethyl, trifluoromethyl, alkyl, aryl, heteroaryl, fluoroalkyl, difluoroalkyl, trifluoroalkyl, polyfluoroalkyl, hydroxyalkyl, or carboxyalkyl.

5. The method of claim 1, wherein the compound is selected from a group consisting of 4-[5-(2,5-di(trifluoromethyl)phenyl)-3-(trifluoromethyl)-1H-pyrazol-1-yl]benzenesulfonamide and 4-[5-(2,5-dibromophenyl)-3-(trifluoromethyl)-1H-pyrazol-1-yl]benzenesulfonamide or an analogue thereof.

6. The method of claim 1, wherein $R_{12}$ is aryl or heteroaryl.

7. The method of claim 6, wherein the compound is N-(3-aminophenyl)-4-(5-(2,5-dimethylphenyl)-3-(trifluoromethyl)-1H-pyrazol-1-yl)benzenesulfonamide.

8. The method of claim 1, wherein the compound is not a COX-2 inhibitor or a histamine-release agent.

9. The method of claim 1, wherein the compound causes the elevation of cytoplasmic calcium concentration significantly above normal level, so as to cause apoptosis in said diseased cells.

10. The method of claim 1, wherein the compound elevates CHOP expression resulting in a condition favorable for initiation of apoptosis in the diseased cells.

11. The method of claim 1, wherein said diseased cells are in a state of ER-stress prior to the administrating step.

12. The method of claim 1, wherein said diseased condition is caused by apoptosis disregulation.

13. The method of claim 1, wherein the cancer is selected from a group consisting of: glioblastoma multiforme, glioma, breast carcinoma, pancreatic carcinoma, Burkett's lymphoma, multiple myeloma, neuroblastoma, prostate cancer, colorectal cancer, recurring cancer, metastatic breast cancer, chemo-resistant tumors, and drug-resistant cancer.

14. The method of claim 1, wherein the cancer cells are chemoresistant tumor cells.

15. The method of claim 1, wherein the cancer cells are endothelial cells.

16. The method of claim 1, wherein the cancer cells are perinecrotic tumor cells.

17. The method of claim 1, further comprising the administration of chemotherapy.

18. The method of claim 17, wherein the cancer is glioma or glioblastoma multiforme, and the chemotherapy treatment includes temozolomide.

19. The method of claim 1, further comprising the administration of radiation therapy.

20. The method of claim 1, further comprising administering a pharmaceutically effective amount of a second compound capable of increasing the concentration of misfolded or damaged proteins in the ER.

21. The method of claim 20, wherein said second compound is a proteasome inhibitor or a protease inhibitor.

22. The method of claim 20, wherein said second compound is selected from a group consisting of: nelfinavir, atazanavir, fosamprenavir, ritonavir, indinavir, or bortezomib or an analogue thereof.

* * * * *